(12) United States Patent
Marks et al.

(10) Patent No.: US 7,964,650 B2
(45) Date of Patent: Jun. 21, 2011

(54) CARBONYL-FUNCTIONALIZED THIOPHENE COMPOUNDS AND RELATED DEVICE STRUCTURES

(75) Inventors: Tobin J. Marks, Evanston, IL (US); Antonio Facchetti, Chicago, IL (US)

(73) Assignee: Northwestern University, Evanston, IL (US)

( * ) Notice: Subject to any disclaimer, the term of this patent is extended or adjusted under 35 U.S.C. 154(b) by 112 days.

(21) Appl. No.: 12/432,063

(22) Filed: Apr. 29, 2009

(65) Prior Publication Data
US 2009/0267061 A1    Oct. 29, 2009

Related U.S. Application Data

(62) Division of application No. 11/227,559, filed on Sep. 14, 2005, now Pat. No. 7,528,176.

(60) Provisional application No. 60/609,678, filed on Sep. 14, 2004.

(51) Int. Cl.
*A61K 31/795* (2006.01)
*C07D 409/14* (2006.01)
(52) U.S. Cl. ...................... 514/772.1; 549/44
(58) Field of Classification Search ................ 549/44; 514/772.1
See application file for complete search history.

(56) References Cited

U.S. PATENT DOCUMENTS

| | | | |
|---|---|---|---|
| 5,834,100 | A | 11/1998 | Marks et al. |
| 6,399,221 | B1 | 6/2002 | Marks et al. |
| 6,585,914 | B2 | 7/2003 | Marks et al. |
| 6,608,323 | B2 | 8/2003 | Marks et al. |
| 6,716,995 | B2 | 4/2004 | Huang et al. |
| 6,723,394 | B1 | 4/2004 | Sirringhaus et al. |
| 6,878,801 | B2 | 4/2005 | Fujiki et al. |
| 6,913,710 | B2 | 7/2005 | Farrand et al. |
| 6,936,190 | B2 | 8/2005 | Yoshida |
| 6,939,625 | B2 | 9/2005 | Marks et al. |
| 6,991,749 | B2 | 1/2006 | Marks et al. |
| 6,998,068 | B2 | 2/2006 | Gerlach |
| 7,029,945 | B2 | 4/2006 | Veres et al. |
| 7,057,054 | B2 | 6/2006 | Irie |
| 7,078,536 | B2 | 7/2006 | Ge et al. |
| 7,081,210 | B2 | 7/2006 | Hirai et al. |
| 7,374,702 | B2 | 5/2008 | Marks et al. |
| 2005/0234256 | A1 | 10/2005 | Marks et al. |
| 2007/0282094 | A1 | 12/2007 | Marks et al. |

OTHER PUBLICATIONS

Afzali et al., "High-Performance, Solution-Processed Organic Thin Film Transistors from a Novel Pentacene Precursor," *J. Am. Chem. Soc.*, 124(30):8812-8813 (2002).
Akimichi et al., "Field-effect transistors using alkyl substituted oligothiophenes," *Appl. Phys. Lett.*, 58(14):1500-1502 (1991).
Bao et al., "High-Performance Plastic Transistors Fabricated by Printing Techniques," *Chem. Mater.*, 9(6):1299-1301 (1997).
Bao et al., "New Air Stable n-Channel Organic Thin Film Transistors," *J. Am. Chem. Soc.*, 120(1):207-208 (1998).
Bao et al., "Printable organic and polymeric semiconducting materials and devices," *J. Mater. Chem.*, 9:1895-1904 (1999).
Bao et al., "Soluble and processable regioregular poly(3-hexylthiophene) for thin film field-effect transistor applications with high mobility," *Appl. Phys. Lett.*, 69(26):4108-4110 (1996).
Bäuerle, *Electronic Materials: The Oligomer Approach*; Müllen et al.; Wiley-VCH: Weinheim, 1998; pp. 105-233.
Brzezinski et al., "A New, Improved and Convenient Synthesis of 4H-Cyclopenta[2,1-b:3,4-b']-dithiophen-4-one," *Synthesis*, 8:1053-1056 (2002).
Castiglioni et al., "Multi-wavelength Raman response of disordered graphitic materials: models and simulations," *Synthetic Metals*, 139:885-888 (2003).
Chesterfield et al., "High Electron Mobility and Ambipolar Transport in Organic Thin-Film Transistors Based on a π-Stacking Quinoidal Terthiophene," *Adv. Mater.*, 15(15):1278-1282 (2003).
Crone et al., "Large-scale complementary integrated circuits based on organic transistors," *Nature*, 403:521-523 (2000).
Dimitrakopoulos et al., "Organic Thin Film Transistors for Large Area Electronic," *Adv. Mater.*, 14(2):99-117 (2002).
Dimitrakopoulos et al., "Organic thin-film transistors: A review of recent advances," *IBM J. Res. Dev.*, 45(1):11-27 (2001).
Dodabalapur et al., "Organic smart pixels," *Appl. Phys. Lett.*, 73(2):142-144 (1998).
Drury et al., "Low-cost all-polymer integrated circuits," *Appl. Phys. Lett.*, 73(1):108-110 (1998).
Facchetti et al., "Building Blocks for n-Type Organic Electronics: Regiochemically Modulated Inversion of Majority Carrier Sign in Perfluoroarene-Modified Polythiophene Semiconductors," *Angew. Chem. Int. Ed.*, 42(33):3900-3903 (2003).
Facchetti et al., "n-Type Building Blocks for Organic Electronics: A Homologous Family of Fluorocarbon-Substituted Thiophene Oligomers with High Carrier Mobility," *Adv. Mater.*, 15(1):33-38 (2003).
Facchetti et al., "Tuning the Semiconducting Properties of Sexithiophene by α,ω-Substitution-α,ω-Diperfluorohexylsexithiophene: The First n-Type Sexithiophene for Thin-Film Transistors," *Angew. Chem. Int. Ed.*, 39(24):4547-4551 (2000).
Garnier et al., "Molecular Engineering of Organic Semiconductors: Design of Self-Assembly Properties in Conjugated Thiophene Oligomers," *J. Am. Chem. Soc.*, 115:8716-8721 (1993).
Groenendaal et al., *Electronic Materials: The Oligomer Approach*; Müllen et al.; Wiley-VCH: Weinheim, 1998; pp. 235-272.
Gruber et al., *Handbook of Advanced Electronic and Photonic Materials and Devices*; Nalwa H.S., Ed.: Academic: San Diego, Calif., 2000; vol. 8, pp. 163-184.
Halik, et al., "Polymer Gate Dielectrics and Conducting-Polymer Contacts for High-Performance Organic Thin-Film Transistors," *Adv. Mater.*, 14(23):1717-1722 (2002).
Halik, et al., "Relationship Between Molecular Structure and Electrical Performance of Oligothiopene Organic Thin Film Transistors," *Adv. Mater.*, 15(11):917-922 (2003).

(Continued)

*Primary Examiner* — Taofiq A Solola
(74) *Attorney, Agent, or Firm* — K&L Gates LLP

(57) ABSTRACT

Carbonyl-functionalized oligo/polythiophene compounds, and related semiconductor components and related device structures.

20 Claims, 10 Drawing Sheets

OTHER PUBLICATIONS

Heidenhain et al., "Perfluorinated Oligo(*p*-Phenylene)s: Efficient n-Type Semiconductors for Organic Light-Emitting Diodes," *J. Am. Chem. Soc.*, 122(41):10240-10241 (2000).

Higuchi et al., "Synthesis and Properties of α,ω-Disubstituted Oligo(3-hexylthiophene)s and Oligothienoquinonoids in Head-to-head Orientation," *Bull. Chem. Soc. Jpn.*, 68:2363-2377 (1995).

Huitema et al., "Active-Matrix Displays Driven by Solution-Processed Polymeric Transistors," *Adv. Mater.*, 14(17):1201-1204 (2002).

Ito et al., "Olgio(2,6-anthrylene)s: Acene-Oligomer Approach for Organic Field-Effect Transistors," *Angew. Chem. Int. Ed.*, 42(10):1159-1162 (2003).

Jackson et al., "Organic Thin-Film Transistors for Organic Light-Emitting Flat-Panel Display Backplanes," *IEEE J. Sel. Top. Quantum Electron.*, 4(1):100-104 (1998).

Kagan et al., "Patterning organic-inorganic thin-film transistors using microcontact printed templates," *Appl. Phys. Lett.*, 79(21):3536-3538 (2001).

Katz et al., "Naphthalenetetracarboxylic Diimide-Based n-Channel Transistor Semiconductors: Structural Variation and Thiol-Enhanced Gold Contacts," *J. Am. Chem. Soc.*, 122(32):7787-7792 (2000).

Katz et al., "Organic field-effect transistors with polarizable gate insulators," *J. App. Phys.*, 91(3):1572-1576 (2002).

Katz et al., "Unsymmetrical *n*-Channel Semiconducting Naphthalenetetracarboxylic Diimides Assembled via Hydrogen Bonds," *Chem. Lett.*, 32(6):508-511 (2003).

Kitamura et al., "Organic Transistor Circuits for Application to Organic Light-Emitting-Diode Displays," *Jpn. J. Appl. Phys.*, 42:2483-2487 (2003).

Klauk et al., "Pentacene organic transistors and ring oscillators on glass and on flexible polymeric substrates," *Appl. Phys. Lett.*, 82(23):4175-4177 (2003).

Kraft, "Organic Field-Effect Transistors—The Breakthrough at Last," *ChemPhysChem*, 2(3):163-165 (2001).

Kunugi et al., "Organic Field-Effect Transistor Using Oligoselenophene as an Active Layer," *Chem. Mater.*, 15(1):6-7 (2003).

Kunugi et al., "Organic Field-Effect Transistors Using Di(2-thienyl)naphthodithiophenes as Active Layers," *Chem. Lett.*, 31(10):958 (2002).

Lee et al., "Pentacene thin film transistors fabricated on plastic substrates," *Synth. Met.*, 139(2):445-451 (2003).

Locklin et al., "Ambipolar Organic Thin Film Transistor-like Behavior of Cationic and Anionic Phthalocyanines Fabricated Using Layer-by-Layer Deposition from Aqueous Solution," *Chem. Mater.*, 15(7):1404-1412 (2003).

Mach et al., "Monolithically integrated, flexible display of polymer-dispersed liquid crystal driven by rubber-stamped organic thin-film transistors," *Appl. Phys. Lett.*, 78(23):3592-3594 (2001).

McCullough, "The Chemistry of Conducting Polythiophenes," *Adv. Mater.*, 10(2):93-116 (1998).

Meng et al., "Oligofluorene-Thiophene Derivatives as High-Performance Semiconductors for Organic Thin Film Transistors," *Chem. Mater.*, 15(9):1778-1787 (2003).

Meng et al., "Tetramethylpentacene: Remarkable Absense of Steric Effect on Field Effect Mobility," *Adv. Mater.*, 15(13):1090-1093 (2003).

Mitzi et al., "Structurally Tailored Organic-Inorganic Perovskities: Optical Properties and Solution-Processed Channel Materials for Thin-Film Transistors," *Chem. Mater.*, 13(10):3728-3740 (2001).

Moratti, *Handbook of Conducting Polyers*; 2$^{nd}$ ed.; Skotheim et al.; Marcel Dekker: New York, 1998; pp. 343-361.

Mushrush et al., "Easily Processable Phenylene-Thiophene-Based Organic Field-Effect Transistors and Solution-Fabricated Nonvolatile Transistor Memory Elements," *J. Am. Chem. Soc.*, 125(31):9414-9423 (2003).

Noh et al., "Organic field-effect transistors by a wet-transferring method," *Appl. Phys. Lett.*, 83(6):1243-1245 (2003).

Pappenfus et al., "A π-Stacking Terthiophene-Based Quinodimethane is an n-Channel Conductor in a Thin Film Transistor," *J. Am. Chem. Soc.*, 124(16):4184-4185 (2002).

Ponomarenko et al., "Star-Shaped Oligothiophenes for Solution-Processible Organic Field-Effect Transistors," *Adv. Funct. Mater.*, 13(8):591-596 (2003).

Reddinger et al., "Molecular Engineering of π-Conjugated Polymers," *Adv. Polymer Sci.*, 145:57-122 (1999).

Renak et al., "Fluorinated Distyrylbenzene Chromophores: Effect of Fluorine Regiochemistry on Molecular Properties and Solid-State Organization," *J. Am. Chem. Soc.*, 121(34):7787-7799 (1999).

Rogers et al., "Printing Process Suitable for Reel-to-Reel Production of High-Performance Organic Transistors and Circuits," *Adv. Mater.*, 11(9):741-745 (1999).

Sheraw et al., "Organic thin-film transistor-driven polymer-dispersed liquid crystal displays on flexible polymeric substrates," *Appl. Phys. Lett.*, 80(6):1088-1090 (2002).

Sirringhaus et al., "High-Resolution Inkjet Printing of All-Polymer Transistor Circuits," *Science*, 290(5499):2123-2126 (2000).

Sirringhaus et al., "Integrated Optoelectronic Devices Based on Conjugated Polymers," *Science*, 280(5370):1741-1744 (1998).

Tsumura et al., "Macromolecular electronic device: Field-effect transistor with polythiophene thin film," *Appl. Phys. Lett.*, 49(18):1210-1212 (1986).

Velu et al., "Low driving voltages and memory effect in organic thin-film transistors with a ferroelectric gate insulator," *Appl. Phys. Lett.*, 79(5):659-661 (2001).

Videlot et al., "Field-Effect Transistors Based on Oligothienylenevinylenes: From Solution π-Dimers to High-Mobility Organic Semiconductors," *Adv. Mater.*, 15(3):306-310 (2003).

Wang et al., "Metal Transfer Printing and its Application in Organic Field-Effect Transistor Fabrication," *Adv. Mater.*, 15(12):1009-1012 (2003).

Wei et al., "Synthesis and Electronic Properties of Aldehyde End-Capped Thiophene Oligomers and Other α,ω-Substituted Sexithiophenes," *Chem. Mater.*, 8(11):2659-2666 (1996).

Würthner, "Plastic Transistors Reach Maturity for Mass Applications in Microelectronics," *Angew. Chem. Int. Ed.*, 40(6):1037-1039 (2001).

Yassar et al., "Cyano-Substituted Oligothiophenes: A New Approach to n-Type Organic Semiconductors," *Adv. Func. Mater.*, 12(10):699-708 (2002).

Facchetti et al., "Electron-Transporting Thiophene-Based Semiconductors Exhibiting Very High Field Effect Mobilities," *Mat. Res. Soc. Symp. Proc.*, 814:331-336 (2004).

CARBONYL-FUNCTIONALIZED THIOPHENE COMPOUNDS AND RELATED DEVICE STRUCTURES

This application is a divisional of prior application U.S. Ser. No. 11/227,559, filed on Sep. 14, 2005 now U.S. Pat. No. 7,528,176, which claims the benefit of and priority to prior provisional application U.S. Ser. No. 60/609,678, filed on Sep. 14, 2004, the entirety of each of which is incorporated herein by reference.

This invention was made with government support under Grant Number NCC-2-1363 awarded by the National Aeronautics and Space Administration (NASA), Grant Number N00014-02-1-0909 awarded by the Office of Naval Research, and Grant Number DMR-0076097 awarded by the National Science Foundation. The government has certain rights in the invention.

BACKGROUND OF THE INVENTION

The formidable building block for the development of (micro)electronics during the last one-half of the century is the field-effect transistor (FET) based on inorganic electrodes, insulators, and semiconductors. These materials have proven to be reliable, highly efficient, and with performance that increases periodically according to the well-known Moore's law. Rather than competing with conventional silicon technologies, an organic FET (OFET) based on molecular and polymeric materials may find large scale applications in low-performance memory elements as well as integrated optoelectronic devices, such as pixel drive and switching elements in active-matrix organic light-emitting diode (LED) displays, RF-ID tags, smart-ID tags and sensors. These systems have been widely pursued since they offer numerous advantages for easy evaporation/solution processing and good compatibility with a variety of substrates including flexible plastics, and great opportunities for facile structural modifications. This trend is driven by the demand for low-cost, large area, flexible, and lightweight devices and the possibility to process these materials at much lower substrate temperatures as compared to the high substrate temperatures for typical inorganic semiconductors.

The simplest and most common OFET device configuration is that of a thin-film transistor (TFT), in which a thin film of the organic semiconductor is deposited on top of a dielectric with an underlying gate (G) electrode. (See FIG. 1, with dimensions for purpose of illustration only; and other configurations are possible.) In the example shown, charge-injecting drain-source (D-S) electrodes providing the contacts are defined either on top of the organic film (top-configuration) or on the surface of the FET substrate prior to the deposition of the semiconductor (bottom-configuration). The current between S and D electrodes is low when no voltage is applied between G and D electrodes, and the device is in the so called 'off' state. When a voltage is applied to the gate, charges can be induced into the semiconductor at the interface with the dielectric layer. As a result, the D-S current increases due to the increased number of charge carriers, providing the 'on' state of a transistor. Key parameters in characterizing a FET are the field-effect mobility ($\mu$) which quantifies the average charge carrier drift velocity per unit electric field and the on/off ratio ($I_{on}$:$I_{off}$) defined as the D-S current ratio between the 'on' and 'off' states. For a high performance OFET, the field-effect mobility and on/off ratio should both be as high as possible.

Most of the OFETs operate in p-type accumulation mode, meaning that the semiconductor acts as a hole-transporting material. However, for the full development of the field, and for organic CMOS devices, high-performing electron-transporting (n-type) materials are needed as well. For most practical applications, the mobility of the field-induced charges should be about 0.1-1 $cm^2$/Vs or greater. To achieve high performance, the organic semiconductors should satisfy stringent criteria relating to both the injection and current-carrying phenomena, in particular: (i) the HOMO/LUMO energies of the individual molecules (perturbed by their placement in a crystalline solid) should be at levels where holes/electrons may be added at accessible applied voltages; (ii) the crystal structure of the material should provide sufficient overlap of the frontier orbitals ($\pi$ stacking and edge-to-face contacts) to allow charge to migrate among neighboring molecules; (iii) the compound should be highly pure since impurities act as charge carrier traps; (iv) the molecules (in particular the conjugated core axes) should be preferentially oriented with their long axes close to the FET substrate normal, as the most efficient charge transport occurs along the direction of intermolecular $\pi$-$\pi$ stacking; and (v) the domains of the crystalline semiconductor should cover uniformly the area between source and drain contacts, hence the film should have a single crystal-like morphology.

Among the organic semiconductors used in OFETs, the class of (oligo, poly)thiophenes are certainly one of the most investigated. The first report on a polyheterocycle-based FET was on polythiophene, and poly(3-hexyl)thiophene and $\alpha,\omega$-dialkyloligothiophenes were the first high-mobility polymer and small molecules, respectively. Over the years, chemical modification(s) of the thiophene core, variations in ring-to-ring connectivity and substitution pattern have resulted in the production and testing of a considerably large number of thiophene-based materials. However, with the exception of very few $\alpha,\omega$-di(cyanomethanide-, perfluorohexyl-, and perfluorophenyl)-substituted nTs, all of these materials are p-type semiconductors.

The synthesis of a large number of fluorocarbon-functionalized oligothiophenes was recently described and compared the molecular/solid-state properties with the corresponding alkyl-substituted and the parent unsubstituted oligothiophenes. All fluorocarbon-substituted oligothiophenes considered had large chemical/thermal stabilities, exhibit similar packing characteristics, strong $\pi$-$\pi$ intermolecular interactions, and comparable LUMO energies across conjugation length. Furthermore, fluoroalkyl functionalization of the nT core significantly alters the electronic, film growth, and semiconducting properties of the resulting films, and that a TFT device with these system as active layer operates in the n-type accumulation mode, indicating facile electron injection into the semiconducting material. In addition, film growth morphologies were shown to strongly depend on growth temperature and substrate functionalization. The field effect mobilities measured in the saturated regime ($V_d$>$V_g$) approach $\approx$0.3 $cm^2$/Vs, the highest reported so far for organic n-type semiconductors. See, U.S. Pat. No. 6,585,914 incorporated herein by reference in its entirety. However, such fluorocarbon substituents limit subsequent structural modification and, in certain environments, present concerns regarding chemical stability.

SUMMARY OF THE INVENTION

Figure 1:
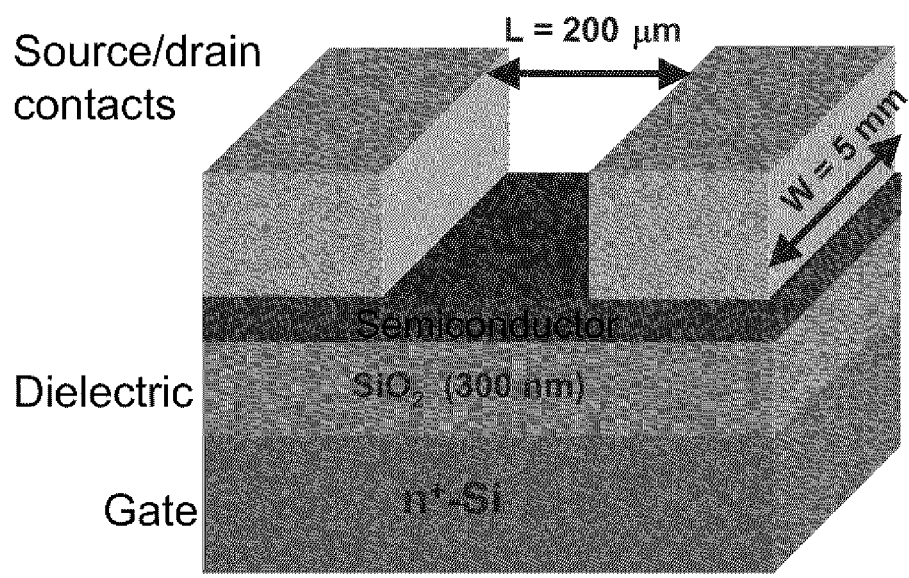
FIG. 1. Schematic diagram of a thin film field effect transistor geometry, known in the art.

In light of the foregoing, it is an object of the present invention to provide a range of compounds and/or related device structures, thereby overcoming various deficiencies and shortcomings of the prior art, including those outlined above. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It is an object of the present invention to provide various oligo/polythiophene compounds exhibiting improved stability and charge transport characteristics.

It can be an object of the present invention to provide one or more compounds having an appropriate functionality, optionally meeting one or more of the aforementioned criteria, for ready incorporation into a conjugated core, and as can be used for possible subsequent chemical modification.

It can be another object of the present invention to provide one or more electrical/transistor devises, including OFET devices, fabricated to comprise a semi-conductor component comprising one or more such compounds, to promote electron mobility or a combination of electron and hole mobilities.

Other objects, features, benefits and advantages of the present invention will be apparent from this summary and the following descriptions of certain embodiments, and will be readily apparent to those skilled in the art having knowledge of various semi-conducting compounds and related device structures. Such objects, features, benefits and advantages will be apparent from the above as taken in conjunction with the accompanying examples, data, figures and all reasonable inferences to be drawn therefrom, alone or with consideration of the references incorporated herein.

In part, this invention can comprise compounds represented by structural formulas I-V, as shown below.

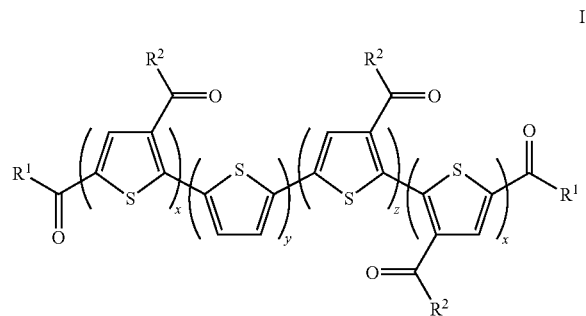

I wherein $R^1$, $R^2$ and $R^3$ can be independently selected from H, alkyl, fluorosubstituted alkyl, aryl, heterocyclic and fluorosubstituted aryl moieties, said alkyl and fluorosubstituted alkyl moieties ranging from about $C_2$ to about $C_{10}$; each said x can be an integer independently ranging from about 0 to about 8; and z can be an integer selected from 0 and integers greater than 0, where at least one of x, y an z can be selected from 2 and integers greater than 2;

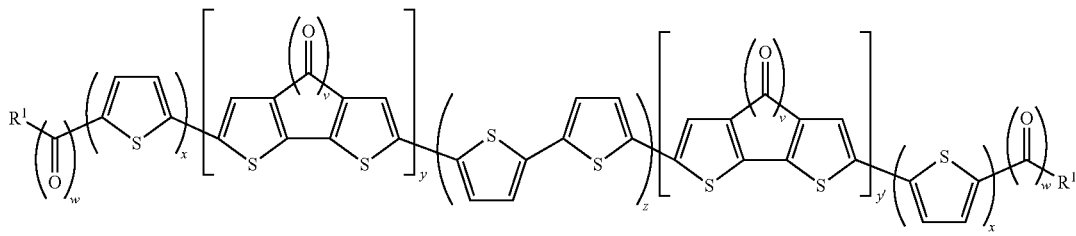

II wherein $R^1$ can be selected from H, alkyl, fluorosubstituted heterocyclic alkyl, aryl and fluorosubstituted aryl moieties, said alkyl and fluorosubstituted alkyl moieties ranging from about $C_2$ to about $C_{10}$; each said x can be an integer independently ranging from 0 to about 4; y and y' can be integers independently selected from 0 to about 4; z can be an integer selected from 0 and integers greater than 0; each said v can be an integer independently selected from 1 and 2; and each said w can be an integer independently selected from 0 and 1, wherein at least one of said x and z can be 1, at least one of y and y' is 1, and at least one of said v and said w is 1; and where v can be 2

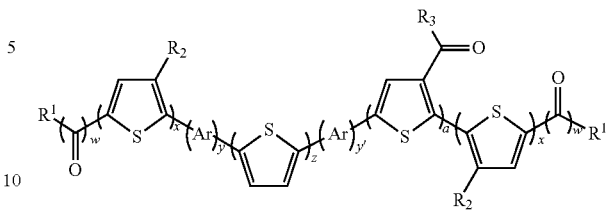

V

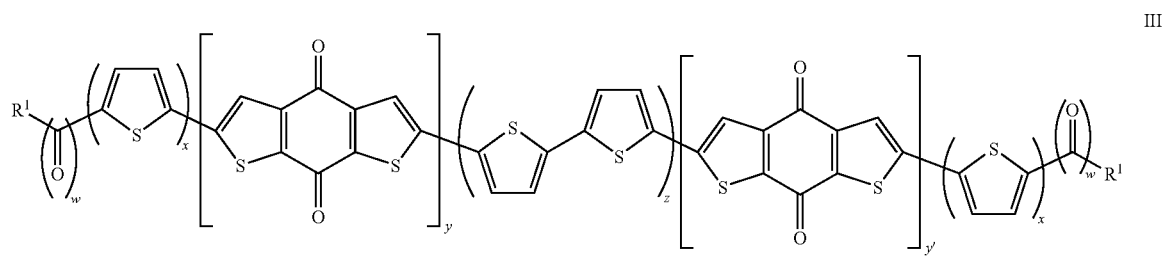

III and where $R^1$ can be fluorosubstituted phenyl

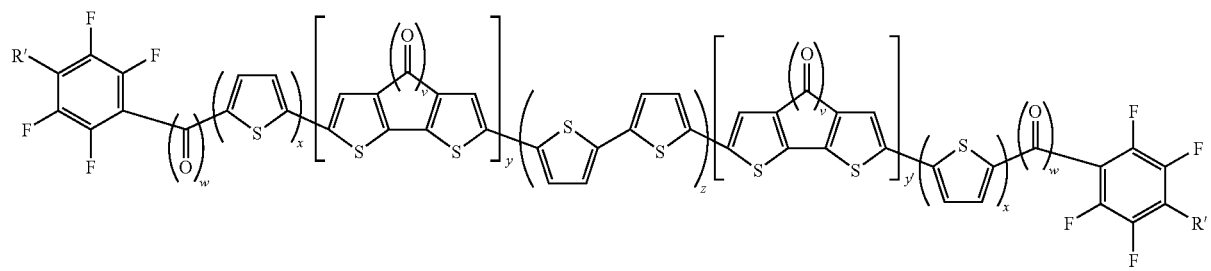

IV

Two representative non-limiting examples of oligothiophene I are shown below: The diperfluorohexyl carbonyl (DFHCO) and dihexyl carbonyl (DHCO) substituted quaterthiophene (4T) compounds Ia and Ib, respectively.

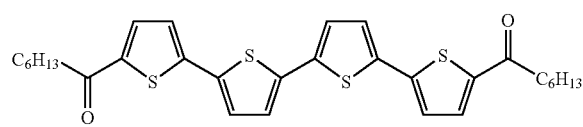

Ia (DFHCO-4T)

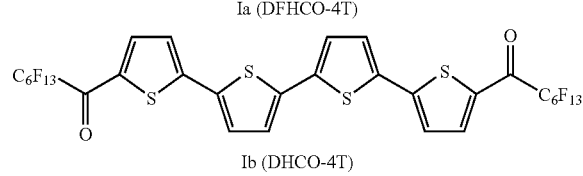

Ib (DHCO-4T)

More generally, the oligothiophene compounds of this invention can be represented by structural formula V, below, where variables corresponding structures I-IV are as described above and Ar can be selected from a y and/or y' number of the aryl and fused aryl (e.g., phenyl and/or thiophenyl) moieties shown in structures II-IV.

wherein $R^1$, $R^2$ and $R^3$ can be independently selected from H, alkyl, fluorosubstituted alkyl, aryl heterocyclic, and fluorosubstituted aryl moieties, said alkyl and fluorosubstituted alkyl moieties ranging from about $C_2$ to about $C_{10}$; each said Ar can be an aryl moiety independently selected from phenyl, perfluorophenyl, diacylphenyl, diacylperfluorophenyl, and thiophenyl moieties; each said x can be an integer independently selected from 0 to about 4; y and y' can be integers independently selected from 0 to about 4; z can be an integer selected from 0 to about 8; and a can be an integer ranging from 0 to about 4, wherein at least one of said x, z and a is selected from 2 and integers greater than 2; and each said w is an integer selected from 0 and 1; and further, $R^2$ can be independently selected from $C(O)R_1$.

Without limitation, in certain embodiments, each of x can be 2, $R_1$ and $R_2$ can be H, y can be 1, y', z, w and a can be 0, and Ar can be diacylperfluorophenyl. A corresponding polymer of such a compound can be of a formula

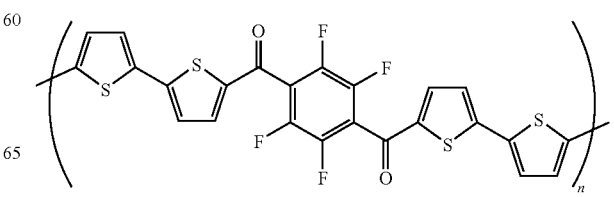

and prepared as discussed more fully below. In certain other embodiments of such compounds/polymers, the 3- and/or 4-positions of one or more thiophenyl moieties can be substituted with alkyl, fluorosubstituted alkyl, and/or fluorosubstituted alkylcarbonyl moieties, such moieties as described above. Likewise, in certain other embodiments, alone or in conjunction with the foregoing, the diacyl moiety can, in the alternative, be phenyl or substituted at one or more positions with one or more other halogen moieties. Such compounds can be used as described below, alone or in combination with one or more other compounds of this invention, in the fabrication of OFET devices—including those comprising semiconductor components comprising one or more of the inventive compounds exhibiting hole mobility, electron mobility, or both under operating conditions.

DETAILED DESCRIPTION OF CERTAIN EMBODIMENTS

The present invention relates to novel classes of thiophene-based materials substituted with one or more carbonyl moieties on the periphery, on the terminal or lateral positions, and at positions along the oligo/polythiophene backbone. With reference to Scheme 1, the choice of any carbonyl moiety of the sort described herein, or understood by those skilled in the art made aware of this invention, can be considered for any one of the following reasons: 1) it is one of the strongest electron-withdrawing groups (EWG), 2) in contrast to e.g., CN and $NO_2$ groups, such a moiety allows additional synthetic modifications/functionalization, 3) it can be part of the π-conjugated core, and 4) it prevents β-elimination of fluorine atoms when positioned in between a fluoroalkyl chain and a carbanion site.

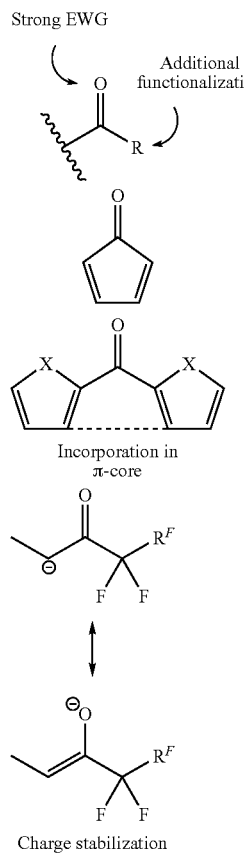

Scheme 1. Effect of Carbonyl Substitution/Insertion.

Figure 2:
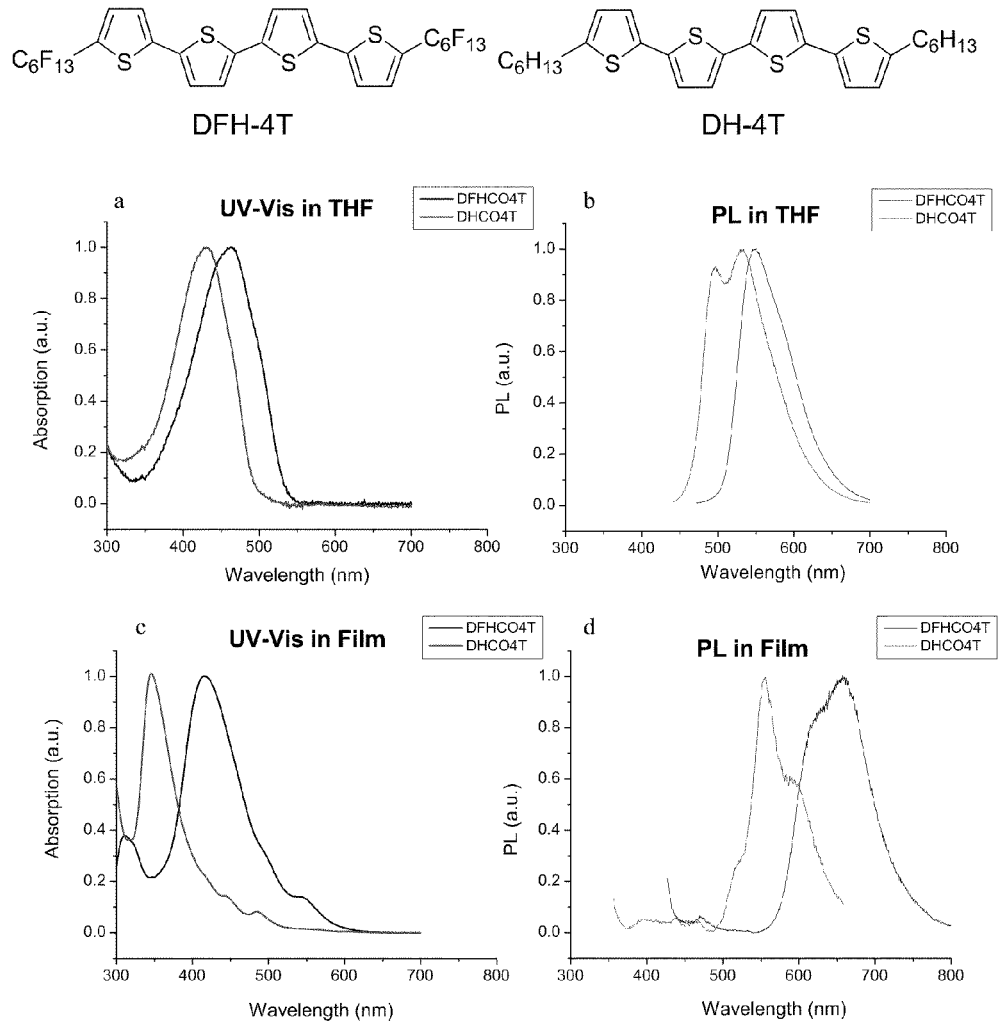
FIGS. 2A-D. UV-vis/PL spectra of Ia (DFHCO-4T) and Ib (DHCO-4T).

The compounds of this invention have been characterized by a combination of techniques including thermal analysis (DSC, TGA), molecular spectroscopy (NMR, UV-Vis, PL), and electrochemistry (CV, DPP). Results confirm that all the thiophene-carbonyl modified systems are more chemically and thermally stable than the corresponding π-isoelectronic olgothiophenes and are highly volatile and soluble in common organic solvents. FIG. 2 shows optical spectrum of THF solution and vacuum-deposited films. These data demonstrate that carbonyl-insertion allows for an effective modulation of optical absorption-emission maximum, optical gap, and photoluminescent efficiencies (quantum yields) both in solution and as thin-deposited films. The effect on the optical spectra is much larger than that found for the corresponding diperfluorohexyl and dihexyl carbonyl-free systems, DFH-4T and DH-4T, whose UV-Vis/PL spectra are almost superimposable.

Table 1 summarizes for purposes of comparison and illustration, the electrochemical data of compounds Ia and Ib to that for the corresponding non-carbonyl compounds of the prior art, DFH-4T and DH-4T. The reduction potential values decease of about 0.7-0.9 V. Reversible oxidation potentials were not observed for the carbonyl series, possibly but without limitation because of the low cation stability.

TABLE 1

Electrochemical data (vs. SCE) for the investigate oligothiophenes.

| | Reduction | | | | | |
|---|---|---|---|---|---|---|
| | Cathodic | | Anodic | | Half | |
| Compound | $E_{c1}$ | $E_{c2}$ | $E_{a1}$ | $E_{a2}$ | $E^{1/2}_1$ | $E^{1/2}_2$ |
| DFH-4T | −1.58 | −1.82 | −1.49 | −1.69 | −1.53 | −1.75 |
| DH-4T | −2.01 | −2.35 | −1.89 | −2.24 | −1.95 | −2.29 |
| DFHCO-4T | −0.93 | −1.04 | −0.83 | −0.97 | −0.88 | −1.01 |
| DHCO-4T | −1.19 | −1.52 | −0.93 | −1.42 | −1.06 | −1.47 |

By combining such electrochemical and optical data, absolute orbital energies can be estimated. LUMO energies can be determined from the first reduction potentials and HOMO energies considering the optical gap. As further shown below, modification of an all-thiophene framework by introduction of powerful carbonyl-containing electron-withdrawing groups was found to decrease MO energy levels, allowing for an easier electron injection. The impact of substitution on the morphology of corresponding thin films and single crystals of several compounds was examined by X-ray crystallography. Depending on chemical nature of the system, deposition method (evaporation, spin-coating, casing), substrate temperature and pretreatment, either highly ordered or amorphous solids can be produced and incorporated into various semi-conductor components and related device structures.

More specifically, several new quaterthiophenes were synthesized according to Scheme 3 and examples 10, 10a-10i, and characterized by conventional chemical and physical methods.

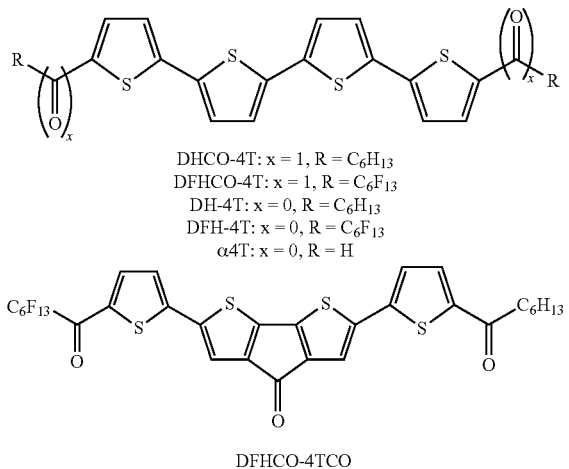

DHCO-4T: x = 1, R = C$_6$H$_{13}$
DFHCO-4T: x = 1, R = C$_6$F$_{13}$
DH-4T: x = 0, R = C$_6$H$_{13}$
DFH-4T: x = 0, R = C$_6$F$_{13}$
α4T: x = 0, R = H

DFHCO-4TCO

Figure 4:
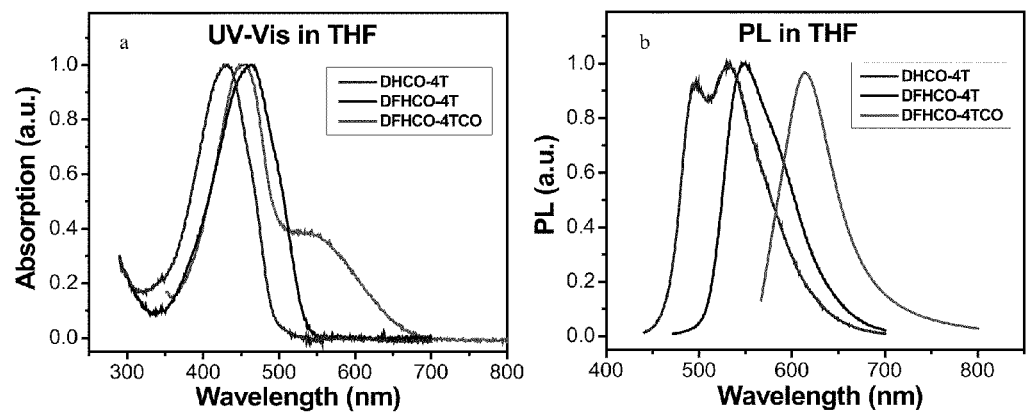
FIGS. 4A-B. UV-vis/Photoluminescence (PL) spectra of DHCO-4T, DFHCO-4T and DFHCO-4TCO.

With reference to examples 10a-10i, cyclic voltammetry (Versus Fc$^+$/Fc (0.54 vs. SCE/THF) using 0.1 M TBAPF$_6$ electrolyte), of 1-3 in THF reveals two reversible one-electron reduction processes [E$_1$/E$_2$ (V): DHCO-4T −1.06/−1.47; DFHCO-4T −0.88/−1.01; DFHCO-4TCO −0.65/−0.78], considerably less negative than unsubstituted α4T (−1.94/−2.07 V). UV-vis/PL data (FIG. 4) indicate that the C=O groups are effectively conjugated with the 4T core, and exhibit substantially red-shifted absorption/emission maxima [λ$_{abs}$/λ$_{em}$ (nm)]: DHCO-4T 430/530; DFHCO-4T 465/550; DFHCO-4TCO 545/615] and HOMO-LUMO gap reductions [E$_g$ (eV): DHCO-4T 2.6; DFHCO-4T 2.4; DFHCO-4TCO 2.2] vs. α4T [λ$_{abs}$/λ$_{em}$=391/450 nm, E$_g$=2.8 eV]. From the electrochemical/optical data HOMO/LUMO energies [E$_{HOMO}$/E$_{LUMO}$ (eV)] are estimated as follows for DHCO-4T (−6.38/−3.78), DFHCO-4T (−6.36/−3.96) and DFHCO-4TCO (−6.39/−4.19) vs. α4T (E$_{HOMO}$/E$_{LUMO}$=−5.79/−2.90 eV). Note that compared to p-type α4T, the new systems exhibit a considerably larger depression of LUMO (~0.9-1.3 eV) vs. HOMO (~0.6 eV) energies, suggesting that carbonyl functionalization of the core should more affect electron than hole transport. In contrast, on going from α4T to DFH-4T (E$_{HOMO}$/E$_{LUMO}$=−6.19/−3.31 eV) or DH-4T (E$_{HOMO}$/E$_{LUMO}$=−5.80/−2.89 eV) a uniform E$_{HOMO}$/E$_{LUMO}$ shift is observed in agreement with σ-EWD substituent effects. Theoretical and experimental studies on carbonyl-functionalized (oligo)heteroaromatics indicate that HOMO energies are less affected than LUMO's, since the latter are more localized on the molecular core. In marked contrast, the LUMO fully extends to the C=O groups via S$_{thiophene}$→C=O intramolecular charge transfer, enhancing substituent σ/π-EWD effects. Therefore, greater perturbation of the 1-3 LUMOs is expected, in excellent agreement with the present electrochemical and optical data.

Figure 5:
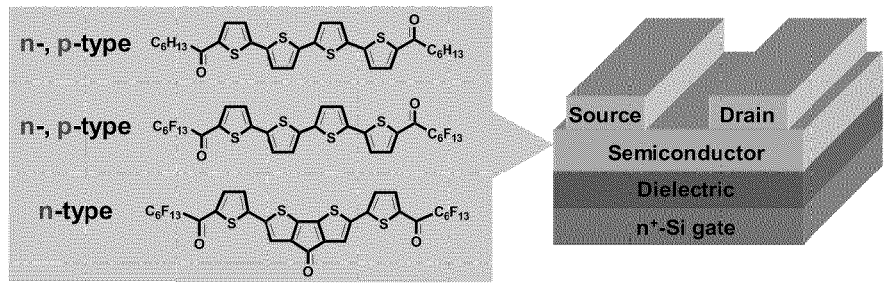
FIG. 5. Schematic diagram of an OFET device, with non-limiting semiconductor compound(s), in accordance with this invention.

Such carbonyl-substituted oligothiophenes are thermally stable and undergo quantitative sublimation. Thin films are readily grown from the vapor phase under vacuum and have been characterized by XRD (revealing molecular edge-on-substrate growth orientation), scanning electron microscopy, and FET I-V measurements. Top-contact FET devices were fabricated as described in the literature and elsewhere herein. Briefly, with respect to examples 10a-10i and 11, semiconductors 1-3 (~50 nm) were vapor-deposited on HMDS-treated p-doped Si/SiO$_2$ substrates maintained at temperatures (T$_D$) between 25-90° C. OFET fabrication was completed by vapor-depositing source-drain Au contacts (~50 nm). (See, schematically, FIG. 5.) Measurements were performed in air and vacuum (~10$^{-5}$ Torr), and the standard saturation FET equation (Eq. 1, below) employed to calculate carrier mobilities.

Figure 6:
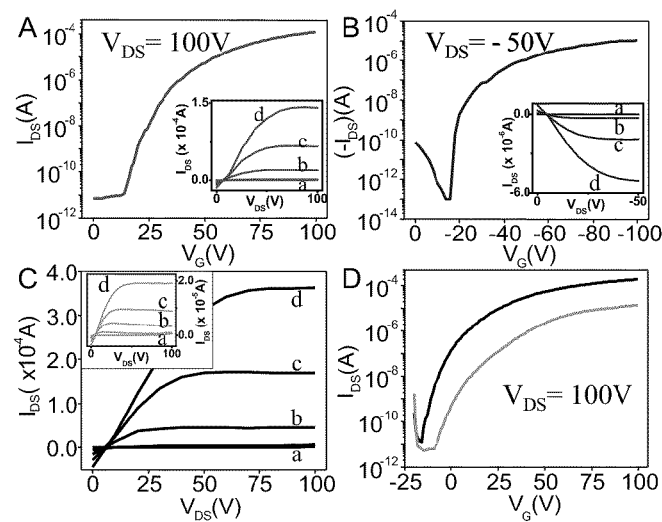
FIGS. 6A-D. $I_{DS}$-V plots for: A. DHCO-4T (n-type, vacuum). B. DHCO-4T (p-type). C. DFHCO-4T in vacuum (black) and air (gray). D. DFHCO-4TCO transfer plots in vacuum (black) and air (light) at different drain-source/gate biases. $V_G(V)$; a=0–±40, b=±60, c=±80, d=±100.
Figure 7:
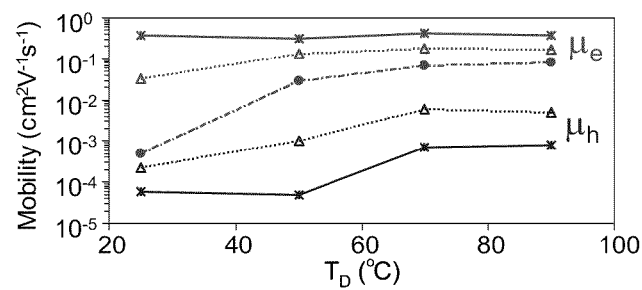
FIG. 7. Electron $\mu_e$ and hole $\mu_h$ mobilities vs. film deposition temperature ($T_D$) for DHCO-4T (Δ), DFHCO-4T (*), and DFHCO-4TCO (•) in vacuum. $\mu_e$ for DFHCO-4T is after $I_2$ vapor treatment.

FIG. 6 shows typical drain-source current-voltage plots for 1-3-based OFETs under different conditions. All of the new oligothiophenes exhibit very high electron mobilities (μ$_e$) in vacuum, with average values as a function of deposition temperature (T$_D$) shown in FIG. 7. For some devices μ$_e$ as high as ~0.65 cm$^2$ V$^{-1}$s$^{-1}$ has been measured. Interestingly, DHCO-4T films also exhibit relatively large hole (i.e., p-type) mobilities (μ$_h$ up to 0.01 cm$^2$V$^{-1}$s$^{-1}$) at all deposition temperatures. Ambipolar transport has been observed previously in blend/bilayers and single component OFETs but with modest figures of merit, large imbalances between μ$_e$ and μ$_h$, and only for narrow T$_D$ ranges. DHCO-4T is the first organic conductor exhibiting unoptimized μ$_e$/μ$_h$ values as high as ~0.1/0.01 cm$^2$V$^{-1}$s$^{-1}$. DFHCO-4T also exhibits ambipolar behavior but only after I$_2$ vapor treatment. More electron-deficient DFHCO-4T and DFHCO-4TCO are air-stable with μ$_e$'s exhibiting the same T$_D$ dependence as in vacuum but with ~5/10× lower magnitudes. Thus, DFHCO-4TCO-based devices can be cycled many times in air without obvious degradation. From the transfer plots, very high I$_{on}$:I$_{off}$ ratios are observed for electrons, >10$^7$. Maximum current gains for holes is >10$^8$ for DHCO-4T. The sub-threshold swings (S), indicating how sharply the devices turn on, are in the 1.3-4.9 V/decade range and turn-on voltages |V$_0$| are ~5-30 V.

Figure 8:
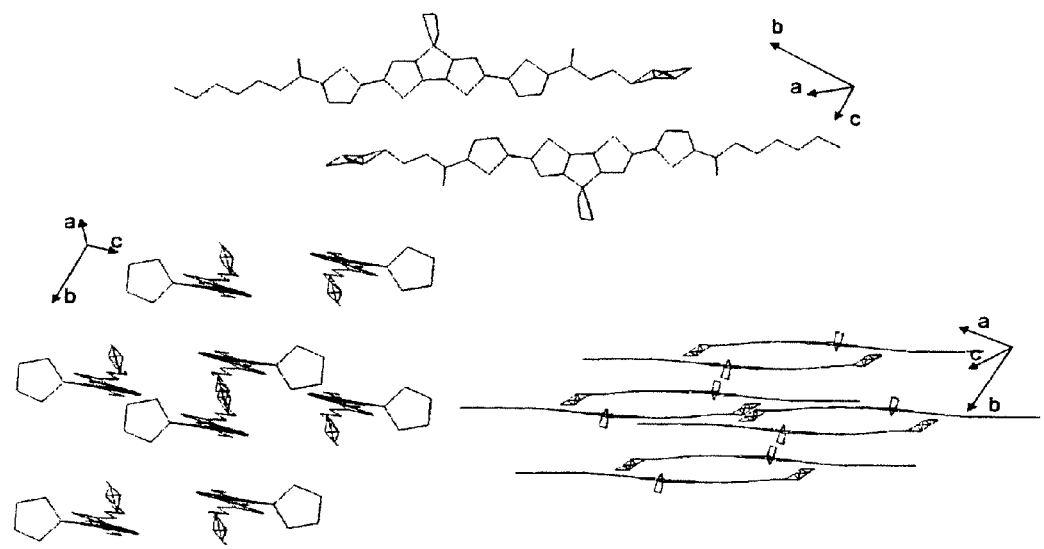
FIG. 8. Illustrations of crystal structure and packing of a dioxolane-protected quaterthiophene.
Figure 9:
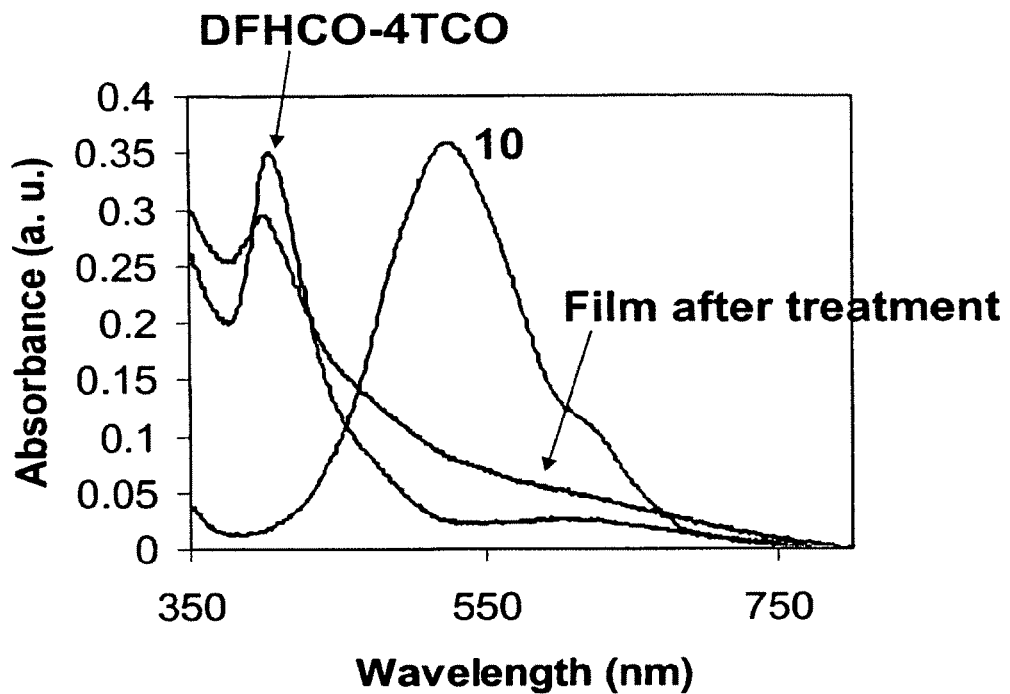
FIG. 9. UV-vis spectra of DFHCO-4TCO and 10 films and that of film 10 after $H_2O$—HCl vapor treatment and annealing.

Solution-processable semiconductors are attractive for low-cost printed electronics applications. Toward that goal, it has been shown that dioxolane-protected quaterthiophenes (e.g., 10, in scheme 3, the precursor of DFHCO-4TCO) exhibit very high solubility in common organic solvents due to reduced π-π core stacking (see crystal structure in FIG. 8). Preliminary results, films of 10 can be readily converted to DFHCO-4TCO films by deprotection via H$_2$O—HCl vapor treatment/annealing (FIG. 9), affording films with μ$_e$~10$^{-4}$ cm$^2$V$^{-1}$s$^{-1}$.

The combination of electron (n-type) materials with hole-transporters (p-type), or concurrent function from one or a combination of materials, will enable inexpensive, high throughput organic CMOS fabrication via spin-coating, drop casting, and/or printing—in contrast to traditional approaches which are high cost, low throughput, and not readily scalable. Two primary challenges exist for achieving such properties: (i) obtaining favorable crystal packing while allowing dissolution by certain solvents, (ii) achieving n-type transport via appropriate molecular electronic structure/orbital energetics and low-defect density films.[3] Post-deposition film processing and chemistries have been explored to address these issues with mixed results, since high purity and highly regular film morphology are essential. As further discussed, below, the present invention provides a new class of soluble oligothiophenes having high electron/hole mobilities both in solution-cast (e.g., μ$_e$~0.25 cm$^2$V$^{-1}$s$^{-1}$) and vapor-deposited (e.g., μ$_e$~0.5 cm$^2$V$^{-1}$s$^{-1}$) films with very high current modulation (e.g., I$_{on}$:I$_{off}$>10$^5$ and 10$^8$, respectively). Furthermore, the structure and energetics of these molecular motifs can also be used as models for the synthesis/characteristics of other n-type polythiophenes, in accordance with this invention.

Figure 10:
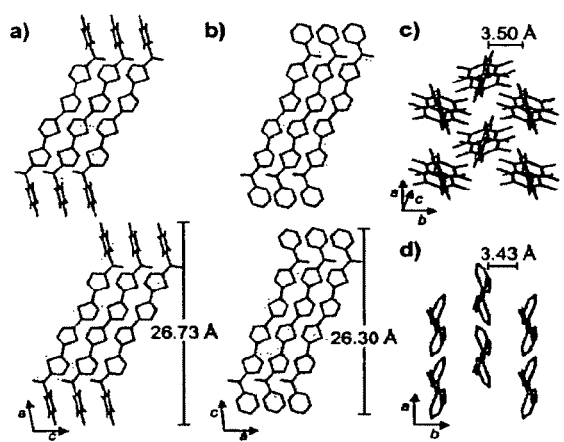
FIGS. 10A-D. With reference to examples 13a-13e, crystal structures of 1 (A) and 2 (B) viewed perpendicular to the long axis of the unit cell (hydrogen atoms not shown). Note the remarkably similar herringbone packing motif in 1 (C) and 2 (D) viewed along the long crystallographic axis.

With reference to examples 13a-13e, below, quaterthiophenes 1 and 2 and polythiophene 3, therein, were synthesized according to Scheme 4 and characterized by conventional chemical and physical methods. Crystals of 1 and 2 suitable for X-ray diffraction were obtained by sublimation. They both crystallize in a herringbone motif (FIG. 10), with the shortest inter-core distance being 3.50 Å (C14-C15) and 3.43 Å (C14-C16), respectively. The average dihedral angle between the phenyl substitutent and the adjacent thiophene subunit is ~53° in 1 and ~49° in 2. The quaterthiophene core of 2 is more planar than that of 1 with a maximum inter-thiophene torsional angle of ~4° versus ~13° in 1. However, the 1 carbonyl groups lie ~6° out of the plane of the adjacent thiophene ring while in 2 this angle increases considerably to ~17°.

Figure 11:
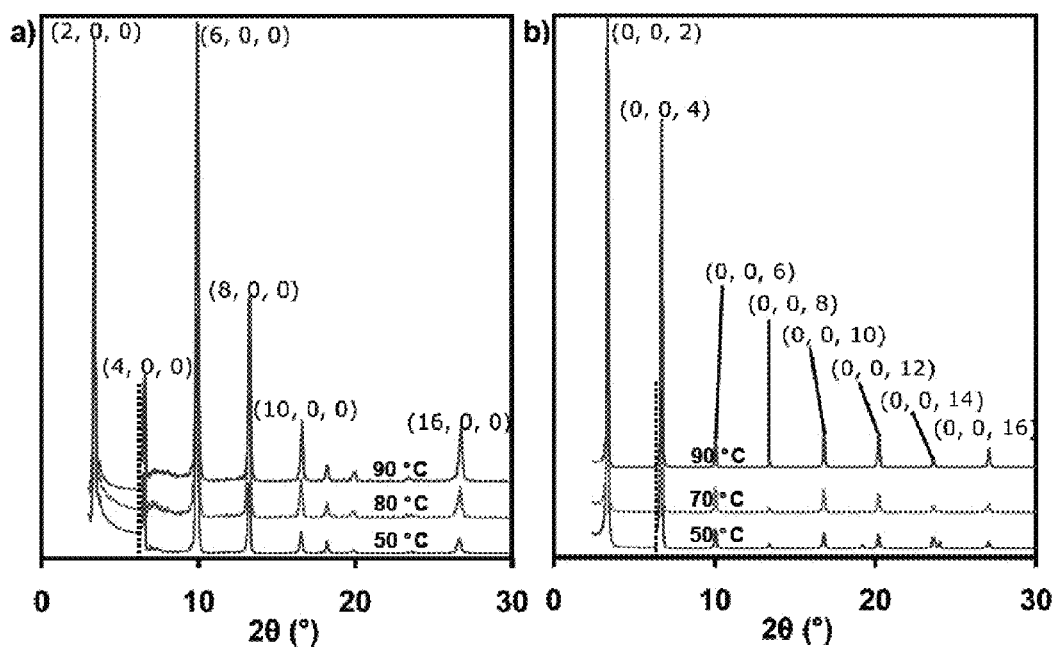
FIGS. 11A-B. Thin film x-ray diffraction patterns of 1 (A) and 2 (B) films vacuum deposited at indicated temperatures onto HMDS treated $SiO_2$ (300 nm)/Si(100) substrates. All data beyond 2θ of 6.4° (dotted line) are expanded by a factor of 10 for clarity. Peaks are assigned from the powder pattern calculated from the single c crystal structures using the program Mercury version 1.3.
Figure 12:
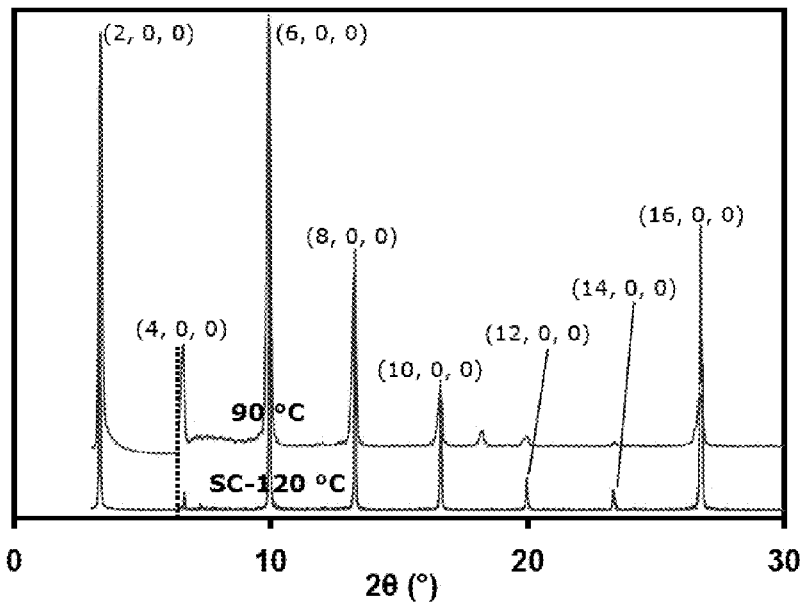
FIG. 12. Thin film x-ray diffraction pattern of 1 solution cast from xylenes (SC-120° C., purple) at 120° C. and vapor-deposited at $T_D$=90° C. (90° C., green) onto HMDS-treated $SiO_2$ (300 nm)/Si(100) substrates. All data beyond 2θ of 6.4° (dotted line) are expanded by a factor of 7 for clarity. Peaks are assigned form the powder pattern calculated form the single crystal structure using the program Mercury version 1.3.

Both semiconductors are thermally stable and undergo quantative sublimation at reduced pressure as indicated by differential scanning calorimetry and thermogravimetric analysis. Films can be grown from the vapor phase and by solution casting from common solvents such as thiophene, toluene, and xylenes. Wide angle x-ray diffraction (WAXRD) indicates that vapor-deposited films are highly crystalline, having the same phase observed in the crystal structure (FIG. 11). The progression of Bragg reflections corresponds to a d-spacing of 27.62 Å (1) and 26.87 Å (2). These spacings are consistent with half of the unit cell long axis (shown in FIG. 10), indicating an end-on-substrate molecular orientation, favorable for in-plane charge transport. As the substrate temperature during vapor phase film deposition ($T_D$) is increased from 25 to 90° C., the films become more crystalline and minority crystallite orientations, present at lower $T_D$, are no longer observable by WAXRD. Diffraction patterns similar to the high $T_D$ vapor-deposited films are also observed for solution deposited films of 1 (FIG. 12).

Figure 13:
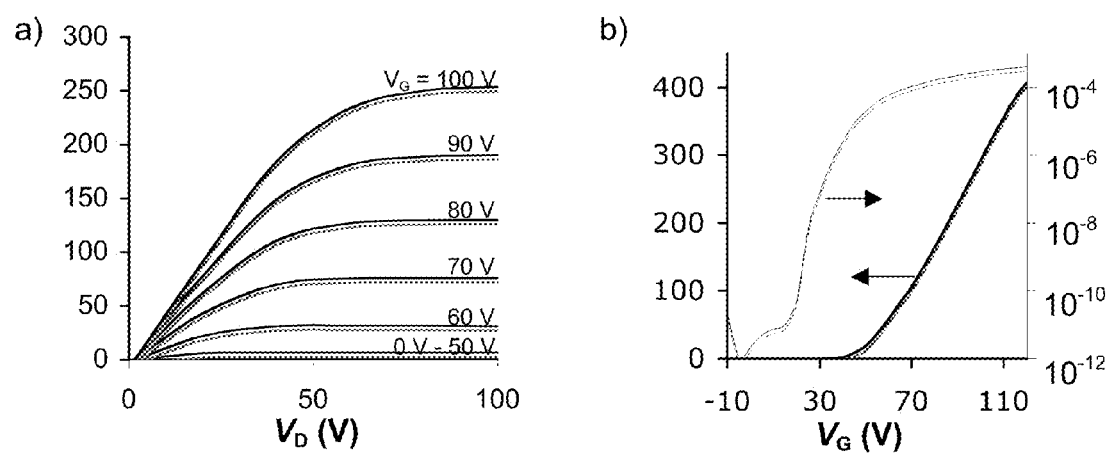
FIGS. 13A-B. Output (A) and transfer (B) plots of an OFET fabricated with 1 vapor deposited at $T_D$=80° C.
Figure 14:
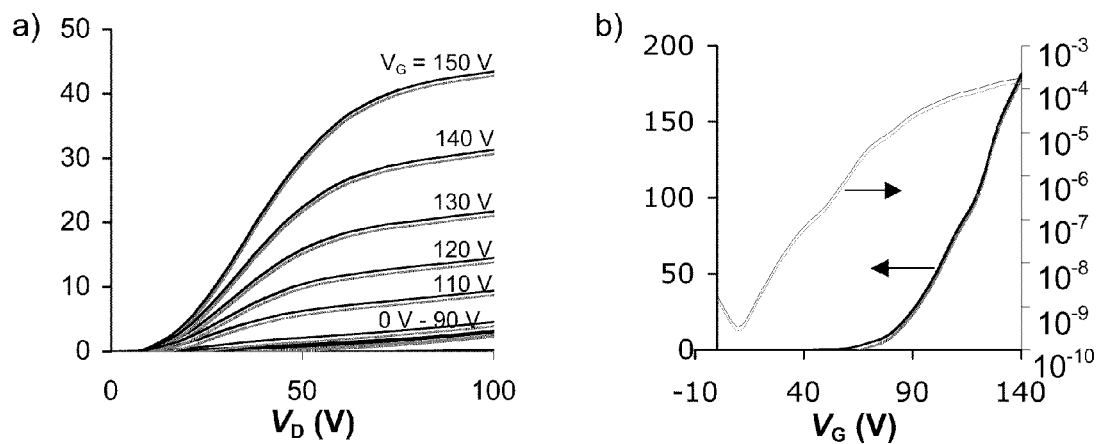
FIGS. 14A-B. Output (A) and transfer (B) plots of an OFET fabricated with 1 solution cast at 120° C.
Figure 15:
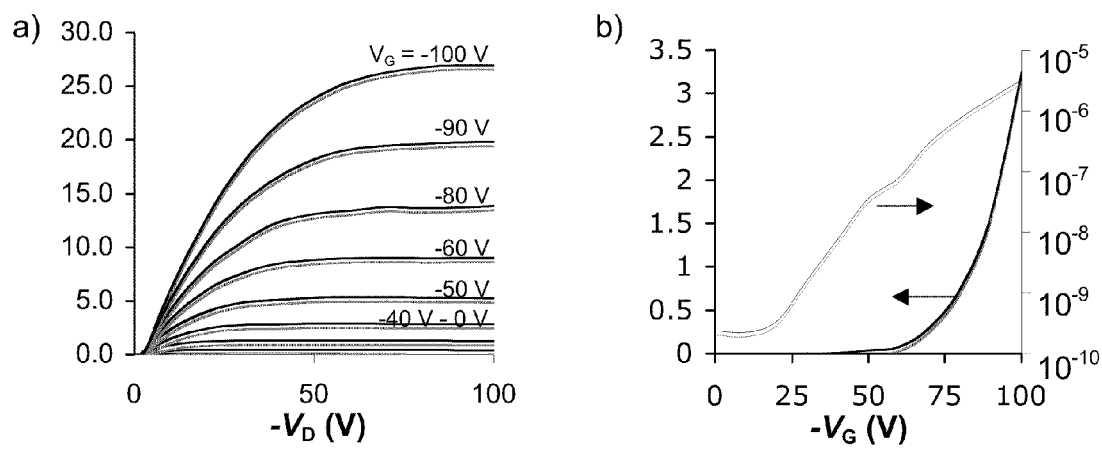
FIGS. 15A-B. Output (A) and transfer (B) plots of an OFET fabricated with 2 vapor deposited at $T_D$=90° C.

As described elsewhere, herein, field effect transistors of 1, 2, and 3 were fabricated with Au top-contact electrodes. Semiconductor films (50 nm) were deposited onto temperature controlled HMDS-treated $SiO_2/p^+$-Si substrates by vapor deposition and drop casting. A 50 nm layer of Au was then deposited through a shadow mask to define the source and drain electrodes. (See example 14.) OFET characterization was preformed in a high vacuum probe station back-filled with Argon. High electron mobilities ($\mu_e$) of ~0.5 $cm^2V^{-1}s^{-1}$ are observed for vapor deposited 1 films ($T_D$=80° C.) with a threshold voltage ($V_T$) of ~30 V ($I_{on}$:$I_{off}$>$10^8$, FIG. 13). This highly reproducible $\mu_e$ value is one of the largest reported to date, doubtless reflecting the favorable crystal packing of this molecule. In solution cast devices, $\mu_e$ is exceptionally high with a maximum of ~0.25 $cm^2V^{-1}s^{-1}$ ($I_{on}$:$I_{off}$=$10^5$; $V_T$=50-70 V, FIG. 14). This is the highest OFET electron mobility for a solution cast semiconductor reported to date, surpassing that of the highest mobility n-type molecular[1n] (0.01 $cm^2V^{-1}s^{-1}$) and polymeric (0.1 $cm^2V^{-1}s^{-1}$) solution processable semiconductors. The non-fluorinated system, 2, exhibits hole mobilities ($\mu_h$) in vapor deposited films up to ~0.04 $cm^2V^{-1}s^{-1}$ ($I_{on}$:$I_{off}$=$10^5$; $V_T$~−20 V, FIG. 15), but no electron conduction is been observed. Films of this material drop-cast from xylenes have $\mu_h$~$3\times10^{-4}$ $cm^2V^{-1}s^{-1}$. Similar dependencies of mobility on $T_D$ are observed in both semiconductors, consistent with the trend, observed by WAXRD, of increased crystallinity with increasing $T_D$.

Figure 16:
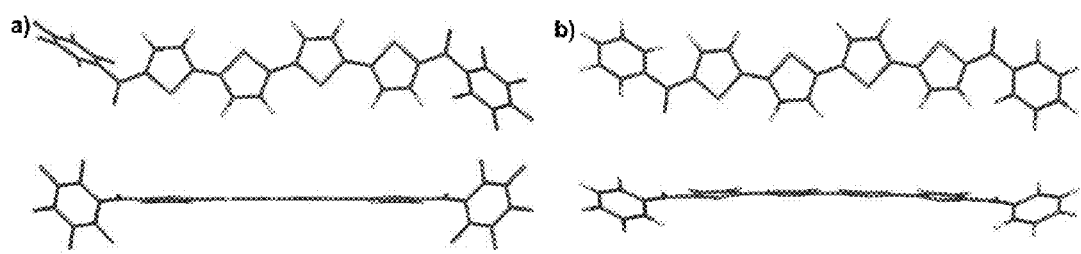
FIGS. 16A-B. Optimized DFT (Q-Chem 2.0‡/DFT/B3LYP/6-31G*) geometries of 1(a) and 2(b) viewed above the plane of the thiophene core (top) and in the thiophene core plane (bottom).

Cyclic voltammetry of the semiconductors in THF reveals two reversible single-electron reductions ($E_1$/$E_2$ (V) vs. S.C.E.) at −1.05/−1.16 in 1 and at −0.95/−1.30 in 2. Irreversible oxidative features are observed at +1.07/+1.22 for 1. UV-vis absorption in THF indicates that the optical band gap ($E_g$) is ~2.40 eV for 1 and ~2.46 eV for 2. Surprisingly, $E_1$ of n-type 1 is slightly more negative (0.1 V) than that of p-type 2. Based upon conventional understanding, redox processes, related to MO energetics, are primary factors in determining majority charge carrier type—therefore, it is surprising that 1 exhibits electron mobility in the solid state, while 2 preferentially conducts holes. Without limitation, an explanation may lie in subtle crystal structure molecular conformational differences—the dihedral angle between the electron-withdrawing carbonyl groups and the thiophene core (intrinsically p-type) is much greater in 2 than in 1. This may be a result of crystal packing forces as the DFT-derived vacuum geometry (FIG. 16) indicates that the carbonyl oxygen lies closer in the thiophene plane for both molecules. The resulting greater conjugation in 1 should enhance stabilization of the negatively charged core in the solid-state. Since such packing effects are not present in solution, the molecular geometry and hence the electronic structure/energetics are more similar—in agreement with MO computation and the electrochemistry experiment.

Finally, polymer 3 (scheme 4, example 13e) is found to have good solubility in common solvents and forms high-quality films when spun cast from xylenes. In THF, 3 undergoes a reversible two electron reduction at −1.23 V plus an additional irreversible reduction at −1.60 V and three single electron oxidations at +0.96/+1.13 V (reversible) and +1.40 V. While spin cast films of the neat polymer exhibit $\mu_e$~$10^{-6}$ $cm^2V^{-1}s^{-1}$ (optimization in progress), an initial study revealed that blends of 1 and 3 (500-1000 ppm, 1:1 wt. ratio from xylenes) yield films with a $\mu_e$ of ~0.01 $cm^2V^{-1}s^{-1}$ ($I_{on}$:$I_{off}$=$10^4$; $V_T$~60 V). Such blends are promising for OFET printing since the polymer adjusts solution rheology, while the molecular semiconductor enhances charge transport.

As discussed above, new carbonyl-functionalized oligo/polythiophenes have been prepared and characterized. A combination of one or more carbonyl substituent(s) affects molecular and solid-state properties and affords materials with unique properties. The results summarized above demonstrate the relationship between connectivity at the molecular level and the collective electro-optical properties of organic solids, and show compounds of this invention, in particular compounds I-V, are extremely useful materials for a range of opto-electronic applications. These materials possess low-lying LUMOs which allow/facilitate electron injection/transport as well as HOMO energies compatible with respectable hole transport. For instance, OFETs fabricated by conventional methods exhibit the largest oligothiophene thin-film $\mu_e$'s found to date and approach the performance of pentacene/$SiO_2$ OFETs.

EXAMPLES OF THE INVENTION

The following non-limiting examples and data illustrate various aspects and features relating to the compounds and/or device structures of the present invention, including preparation of n-type thiophene semiconductor compounds, as are available through the synthetic methodologies described herein and by incorporated reference. In comparison with the prior art, the present compounds and related devices provide results and data which are surprising, unexpected and contrary thereto. While the utility of this invention is illustrated through the use of several compounds and related semiconductor components made therefrom, it will be understood by those skilled in the art that comparable results are obtainable with various oligo/poly compounds and/or semiconductor components, as are commensurate with the scope of this invention.

Example 1

Generally, 2-Thiophenylaldehyde and 2-bromothiophene are commercially available. The reagent 5,5'-bis(tri-b-butyl-stannyl)-2,2'-dithiophene was prepared according to the known procedure (Wei, Y.; Yang, Y.; Yeh, J,-M. *Chem. Mater.*

1996, 8, 2659). With reference to Scheme 2 and examples 2-7, compounds 1-4 are prepared as described below, enroute to the diperfluorohexyl and dihexyl compounds, DFHCO-4T and DHCO-4T, respectively.

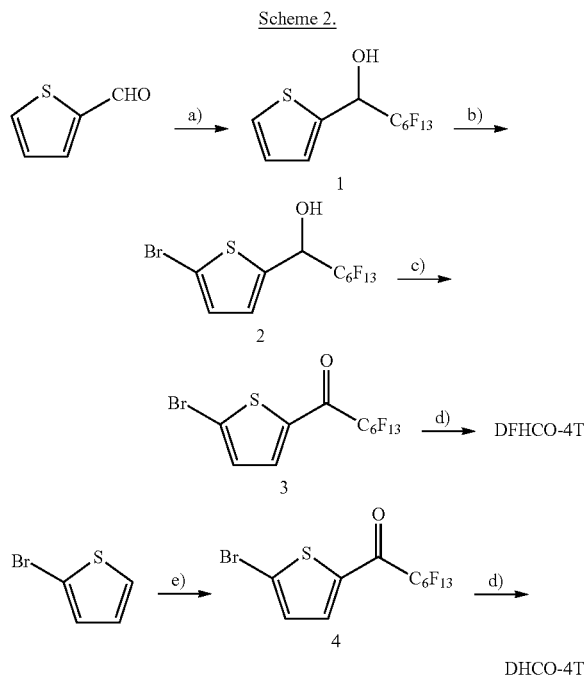

Scheme 2.

a) $C_6F_{13}I$, MeLi, $Et_2O$, $-78°$ C.; HCl.
b) $Br_2$, $CH_2Cl_2$. (c) $MnO_2$, $CH_2Cl_2$.

d) 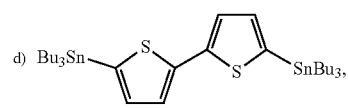

Pd[PPh$_3$]$_4$, DMF, 100° C., N$_2$. (e) $C_6H_{13}COCl$, AlCl$_3$, benzene, reflux.

While the synthetic techniques schematically illustrated here are provided with reference to the compounds of examples 1-7, analogous procedures or variations thereof—as provided elsewhere herein—can be used or modified as would be understood by those skilled in the art en route to other carbonyl substituted/functionalized oligo/poly-thiophenes, in accordance with this invention.

Example 2

Perfluorohexyl-thien-2-yl-methanol (1). 1.6 M MeLi (15.9 mL) was added dropwise to a solution of 5-thiophenyl aldehyde (2.80 g, 25.0 mmol) and perfluorohexyliodide (11.73 g, 26.3 g) in dry $Et_2O$ (70 mL) at $-78°$ C. with stirring. The mixture was stirred for additional 40 min and quenched with 3N HCl (70 mL). The organic layer was separated, washed with water twice, dried over $MgSO_4$, and concentrated in vacuo. Column chromatography of the residue over silica gel (hexane:ethyl acetate=1:1) yielded 1 (6.20 g, 57%).

Example 3

Perfluorohexyl-(5-bromothien-2-yl)-methanol (2). Bromine (0.698 g) was added to a solution of 1 (1.80 g, 4.16 mmol) in $CH_2Cl_2$ (15 mL). After stirring overnight at room temperature, the mixture was neutralized with saturated aqueous $NaHCO_3$ solution and extracted with $CH_2Cl_2$ (3×20 mL). The organic layers were combined, dried over $MgSO_4$, and concentrated in vacuo (1.90 g, 89%).

Example 4

2-Perfluorohexylcarbonyl-5-bromothiophene (3). A $CH_2Cl_2$ solution of compound 2 (1.90 g, 3.72 mmol) and activated $MnO_2$ (5 g) was stirred overnight. The mixture was filtered with celite. The filtrate was dried over $MgSO_4$, and the solvent was evaporated in vacuum (1.85 g, 98%).

Example 5

5,5'''-Diperfluorohexylcarbonyl-2,2':5',2'':5'',2'''-quater-hiophene, DFHCO-4T, (Ia). A mixture of compound 3 (1.86 g, 3.66 mmol), 5,5'-bis(tri-b-butylstannyl)-2,2'-dithiophene (1.36 g, 1.83 mmol), and tetrakis(triphenylphosphine)palladium(0) (0.13 g, 0.11 mmol) in dry DMF (10 mL) was deaerated three times with $N_2$. The reaction mixture was stirred overnight at 100° C. during which time a precipitate formed. After cooling, the dark red solid was collected by filtration and washed several times with hexane, MeOH. Further purification was achieved by gradient vacuum sublimation (1.22 g, 65%). Elemental Analysis calcd for $C_{30}H_8F_{26}O_2S_4$ (%): C, 35.24; H, 0.79; F, 48.30; found: C, 35.13; H, 0.84; F, 48.51; MS (EI): m/z (%) 1021.5 (100) [M$^+$].

Example 6

2-Heptanoyl-5-bromothiophene (4). 2-Bromothiophene (1.63 g, 10.0 mmol) and heptanoyl chloride (1.78 g, 12.0 mmol) were dissolved in dry benzene (15 mL) and $AlCl_3$ was added in portions with stirring over 10 min. The resulting dark brown solution was refluxed for 1 hr and left to cool down to room temperature. The mixture was quenched with 2M HCl (15 mL) carefully while stirred. The organic layer was separated, washed with 2M HCl, 2M NaOH, and water, and passed through silica column (d=3 cm, l=8 cm). The solution was dried over $MgSO_4$, and concentrated in vacuo (2.40 g, 87%).

Example 7

5,5'''-Diheptanoyl-2,2':5',2'':5'',2'''-quaterhiophene, DHCO-4T, (Ib). A mixture of compound 4 (0.64 g, 2.33 mmol), 5,5'-bis(tri-b-butylstannyl)-2,2'-dithiophene (0.744 g, 1.00 mmol), and tetrakis(triphenylphosphine)palladium(0) (0.07 g, 0.06 mmol) in dry DMF (5 mL) was deaerated three times with $N_2$. The reaction mixture was stirred overnight at 100° C. during which time a precipitate formed. After cooling, the orange solid was collected by filtration and washed several times with hexane, MeOH. The solid was recrystallized in xylene and dried in vacuum oven (120° C.) yielding pure compound (0.36 g, 65%). Elemental Analysis calcd for $C_{30}H_{34}O_2S_4$ (%): C, 64.94; H, 6.18; found: C, 64.80; H, 6.21; MS (EI): m/z (%) 553.9 (100) [M$^+$].

Example 8

In accordance with the preceding and following examples, various other carbonyl-functionalized (e.g., heterocylacyl, etc.) oligothiophene compounds of structures I-IV and/or V can be prepared using synthetic techniques of the sort described in the aforementioned incorporated '914 patent or straight-forward modifications thereof, depending upon choice of reagent or thiophene core, as would be understood by those skilled in the art made aware of this invention.

Example 9

Field effect transistor devices were fabricated for compounds of the preceding examples using a top-contact configuration. These semiconductors were vacuum-deposited on top of HMDS-treated Si/SiO$_2$ substrates kept at the temperature (T$_D$) of 25 and 70° C. To show the precision of each measurement, the reported data are an average of at least three devices tested at different area of the semiconductor layer.

Example 10

With respect to Scheme 3, below, and examples 10a-10i and 11, the reagent 2-thiophenylaldehyde and 2-bromothiophene are commercially available. The reagent 5,5'-bis(tri-b-butylstannyl)-2,2'-dithiophene was prepared according to the known procedure (Wei, Y.; Yang, Y.; Yeh, J.-M. *Chem. Mater.* 1996, 8, 2659). Compound 8 was prepared following a known procedure (Brzezinski, J. Z.; Reynolds, J. R. *Synthesis* 2002, 8, 1053, respectively).

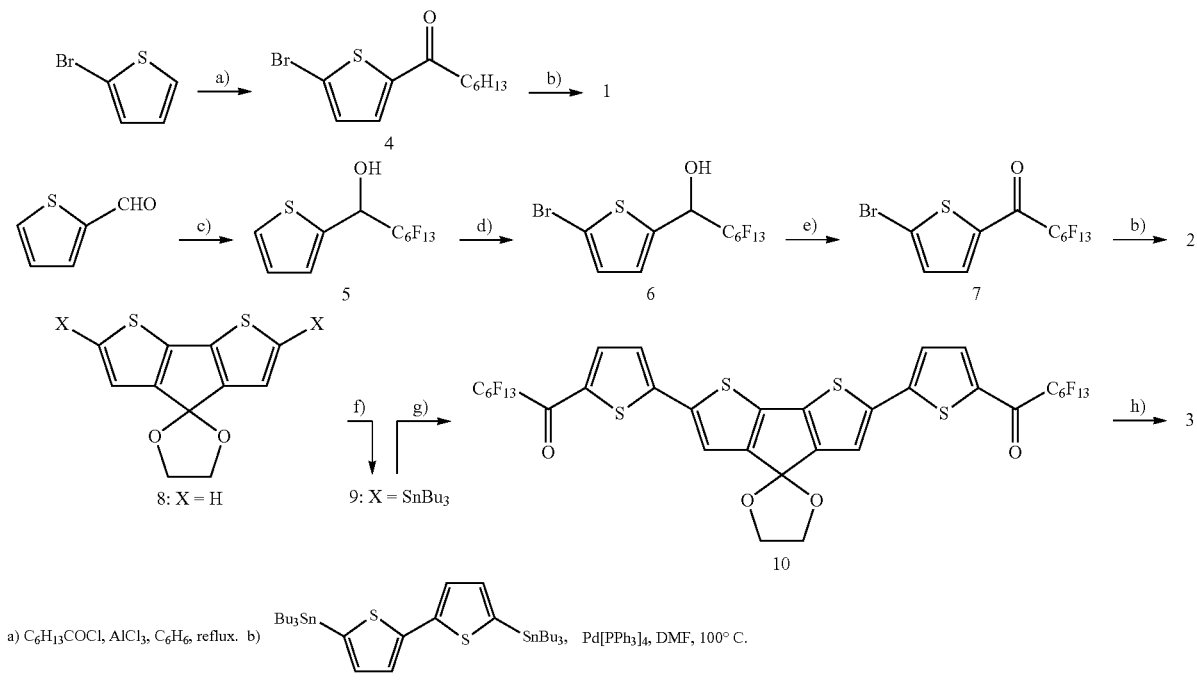

Scheme 3. Synthetic route to semiconductors 1-3, below.

a) C$_6$H$_{13}$COCl, AlCl$_3$, C$_6$H$_6$, reflux. b) Pd[PPh$_3$]$_4$, DMF, 100° C.
c) C$_6$F$_{13}$I, MeLi, Et$_2$O, -78° C.; HCl. d) Br$_2$, CH$_2$Cl$_2$. e) MnO$_2$, CH$_2$Cl$_2$.
f) n-BuLi, Bu$_3$SnCl g) 7, Pd[PPh$_3$]$_4$, DMF, 90° C. h) AcOH—HCl, reflux.

Figure 3:
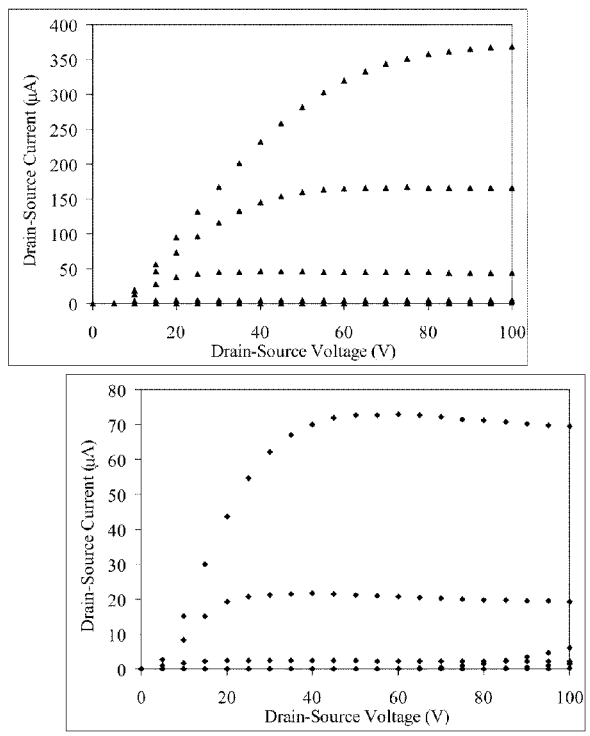
FIG. 3. FET current-voltage characteristics of Ia and Ib under different positive gate-source biases (e.g., OV, 80V and 100V).

The electrical measurements were performed under vacuum (~10$^{-4}$ Torr). FIG. 3 shows typical drain-source current/voltage plots of compounds Ia and Ib operating at different gate bias. For the purposes of comparison with other organic FETs, the mobilities were calculated by standard field effect transistor equations. In traditional metal-insulator-semiconductor FETs (MISFETs) there is typically a linear and saturated regime in the I$_{DS}$ VS V$_{DS}$ curves at different V$_G$. At large V$_{DS}$ the current saturates and is given by equation (1)

$$(I_{DS})_{sat} = (WC_i/2L)\mu(V_G - V_t)^2 \quad (1)$$

where L and W are the device channel length and width, respectively, C$_i$ is the capacitance of the insulator (1×10$^{-8}$ F/cm$^2$ for 300 nm SiO$_2$). The mobility and the threshold voltage (V$_t$) can be calculated from the slope and intercept, respectively, of the linear section of the plot of V$_G$ versus (I$_{sd}$)$^{1/2}$ (at V$_{sd}$=-100 V). FIG. 3 shows I-V electrical characteristics of Ia and Ib. From these data n-type mobilities approaching 0.5 cm$^2$/Vs, current on/off ratio of 10$^6$-10$^7$, and Vt of ~20V were obtained. Furthermore, devices of Ib exhibit ambipolar characteristics, meaning that a channel of both electrons and holes can be induced upon applying a positive and negative bias to the gate-source contacts, respectively.

Example 10a

Synthesis of 5,5'''-diheptanoyl-2,2':5',2'':5'',2'''-quaterhiophene (DHCO-4T, 1). A mixture of compound 4 (0.64 g, 2.33 mmol), 5,5'-bis(tri-n-butylstannyl)-2,2'-dithiophene (0.744 g, 1.00 mmol), and tetrakis(triphenylphosphine)palladium(0) (0.07 g, 0.06 mmol) in dry DMF (5 mL) was deaerated three times with N$_2$. The reaction mixture was stirred overnight at 100° C. during which time a precipitate formed. After cooling, the orange solid was collected by filtration and washed several times with hexane, then MeOH. The solid was recrystallized from xylene and dried in vacuum oven (120° C.) yielding pure compound (0.36 g, 65%). mp 290° C.; $^1$H NMR (CD$_2$Cl$_2$) δ 7.60 (d, 2H, $^2$J=3.6 Hz), 7.25 (d, 2H, $^2$J=3.6 Hz), 7.19 (d, 2H, $^2$J=3.6 Hz), 7.16 (d, 2H, $^2$J=3.6 Hz), 2.85 (t, 4H, $^3$J=7.6 Hz), 1.72-1.70 (m, 4H), 1.36-1.31 (m, 12H), 0.88 (t, 4H, $^3$J=6.0 Hz); Anal. Calcd for C$_{30}$H$_{34}$O$_2$S$_4$: C, 64.94; H, 6.18. Found: C, 64.80; H, 6.21; MS (EI): m/z (%) 553.9 (100) [M$^+$].

Example 10b

Synthesis of 5,5'''-diperfluorohexylcarbonyl-2,2':5',2'':5'',2'''-quaterhiophene (DFHCO-4T, 2). A mixture of compound 3 (1.86 g, 3.66 mmol), 5,5'-bis(tri-b-butylstannyl)-2,2'-dithiophene (1.36 g, 1.83 mmol), and tetrakis(triphenylphosphine)palladium(0) (0.13 g, 0.11 mmol) in dry DMF (10 mL) was deaerated three times with $N_2$. The reaction mixture was stirred overnight at 100° C. during which time a precipitate formed. After cooling, the dark red solid was collected by filtration and washed several times with hexane, then MeOH. Further purification was achieved by gradient vacuum sublimation (1.22 g, 65%). mp 248° C.; $^1$H NMR ($CD_2Cl_2$) 120° C. δ 7.93 (2H), 7.39 (2H), 7.32 (2H), 7.27 (2H); $^{19}$F NMR ($CD_2Cl_2$) 120° C. δ −79.88 (6F), −113.42 (4F), −120.18 (8F), −121.62 (4F), −124.90 (4F). Anal. Calcd for $C_{30}H_8F_{26}O_2S_4$: C, 35.24; H, 0.79; F, 48.30. Found: C, 35.13; H, 0.84; F, 48.51; MS (EI): m/z (%) 1021.5 (100) [M$^+$].

Example 10c

Synthesis of 2,7-[bis-(5-perfluorohexylcarbonylthien-2-yl)]-4H-cyclopenta[2,1-b:3,4-b]-dithiophen-4-one (DFHCO-4TCO, 3). Molecule 7 (0.50 g, 0.46 mmol) was dissolved in 75 mL acetic acid while refluxing. After addition of concentrated HCl (2 mL), the solution turned from purple to brown, and a dark green precipitate formed immediately. The reaction was quenched with $H_2O$ (20 mL). The solution was then decanted off while warm and the product was collected as a dark green solid (0.45 g). The solid was washed with acetone (2×10 mL) and chloroform (6×10 mL), dried overnight in vacuum oven, and purified by gradient sublimation twice. The pure portion was collected and washed with boiling chloroform (20 mL). The red solution was decanted leaving the product as a black solid. It was washed with chloroform and purified by gradient sublimation (0.265 g, 60% yield): mp 297° C.; Anal. Calcd for $C_{31}H_6F_{26}O_3S_4$: C, 35.51; H, 0.58. Found: C, 35.40; H, 0.71; MS (EI, 70 eV) m/z: calcd (M$^+$) for $C_{31}H_6F_{26}S_4O_3$, 1048.0; found, 1048.0.

Example 10d

Synthesis of 2-heptanoyl-5-bromothiophene (4). The reagent of 2-bromothiophene (1.63 g, 10.0 mmol) and heptanolyl chloride (1.78 g, 12.0 mmol) were dissolved in dry benzene (15 mL) and $AlCl_3$ was added in portions with stirring over a period of 10 min. The resulting dark brown solution was refluxed for 1 h and left to cool down to room temperature. The reaction mixture was quenched with 2M HCl (15 mL) while carefully stirring. The organic layer was separated, washed with 2M HCl, 2M NaOH, and water, and passed through silica column (d=3 cm, l=8 cm). The collected solution was dried over $MgSO_4$, and concentrated in vacuo (2.40 g, 87%). $^1$H NMR ($CDCl_3$): δ 7.44 (d, 1H, $^2$J=3.8 Hz), 7.10 (d, 1H, $^2$J=3.8 Hz), 2.81 (t, 2H, $^3$J=7.4 Hz), 1.74-1.68 (m, 2H), 1.38-1.23 (m, 6H), 0.89 (t, 3H, $^3$J=6.4 Hz); HRMS (EI, 70 eV) m/z: calcd (M$^+$) for $C_{11}H_{15}BrOS$, 274.00; found, 274.0016.

Example 10e

Synthesis of perfluorohexyl-thien-2-yl-methanol (5). MeLi (1.6 M, 15.9 mL) was added dropwise to a solution of 5-thiophenyl aldehyde (2.80 g, 25.0 mmol) and perfluorohexyliode (11.73 g, 26.3 g) in dry $Et_2O$ (70 mL) at −78° C. with stirring. The mixture was stirred for additional 40 min and quenched with 3N HCl (70 mL). The organic layer was separated, washed with water twice, dried over $MgSO_4$, filtered, and concentrated in vacuo. Column chromatography of the residue over silica gel (hexane:ethyl acetate=1:1) yielded 5 (6.20 g, 57%). $^1$H NMR ($CDCl_3$): δ 7.45 (d, 1H, $^2$J=4.5 Hz), 7.24 (d, 1H, $^2$J=3.0 Hz), 7.10-7.06 (dd, 1H, J=4.5, 3.8 Hz), 5.54-5.46 (m, 1H), 2.56 (d, 1H, $^2$J=5.7 Hz); HRMS (EI, 70 eV) m/z: calcd (M$^+$) for $C_{11}H_5F_{13}OS$, 431.99; found, 431.9838.

Example 10f

Synthesis of perfluorohexyl-(5-bromothien-2-yl)-methanol (6). Bromine (0.698 g, 4.37 mmol) was added to a solution of 1 (1.80 g, 4.16 mmol) in $CH_2Cl_2$ (15 mL). After stirring overnight at room temperature, the mixture was neutralized with saturated aqueous $NaHCO_3$ solution and extracted with $CH_2Cl_2$ (3×20 mL). The organic layers were combined, dried over $MgSO_4$, filtered, and concentrated in vacuo (1.90 g, 89%). $^1$H NMR ($CDCl_3$): δ 7.02 (d, 1H, $^2$J=3.7 Hz), 6.97 (d, 1H, $^2$J=3.8 Hz), 5.46-5.38 (m, 1H), 2.64 (d, 1H, $^2$J=5.2 Hz); HRMS (EI, 70 eV) m/z: calcd (M$^+$) for $C_{11}H_4F_{13}BrOS$, 509.90; found, 509.8945.

Example 10g

Synthesis of 2-perfluorohexylcarbonyl-5-bromothiophene (7). A solution of compound 2 (1.90 g, 3.72 mmol) and activated $MnO_2$ (5 g) was stirred overnight. The mixture was filtered through Celite. The filtrate was dried over $MgSO_4$, and the solvent evaporated in vacuum (1.85 g, 98%). The mixture was purified by sublimation; mp 27° C.; $^1$H NMR ($CDCl_3$): δ 7.74 (d, 1H, $^2$J=3.8 Hz), 7.23 (d, 1H, $^2$J=3.8 Hz); $^{19}$F NMR ($CDCl_3$) δ −81.20 (3F), −115.20 (2F), −121.77 (4F), −123.18 (2F), −126.53 (2F); Anal. Calcd for $C_{11}H_2BrF_{13}OS$: C, 25.95; H, 0.40. Found: C, 26.11; H, 0.54; MS (EI, 70 eV) m/z: (M$^+$) calcd for $C_{11}H_2BrF_{13}OS$ 509.8; found 509.8.

Example 10h

Synthesis of spiro[4H-cyclopenta[2,1-b:3,4-b']dithiophene-4,2'-[1,3]dioxolane], 2,6-bis(tri-n-butylstannyl) (9). Spiro[4H-cyclopenta[2,1-b:3,4-b']dithiophene-4,2'-[1,3]dioxolane] (1.71 g, 7.35 mmol) was dissolved in dry THF (20 mL) under nitrogen and cooled to −78° C. Two equivalents of n-BuLi were added dropwise (5.92 mL, 14.85 mmol) and the reaction mixture stirred for 30 min. The solution was allowed to warm to room temperature and stirred for an additional 1.5 h. The resulting thick brown suspension was cooled again to −78° C. and tri-n-butyltin chloride (4.78 g, 14.7 mmol) was added. The solution was then stirred at room temperature for 4 h. The reaction was quenched with 100 mL $H_2O$ and extracted with hexane. The organic layer was washed with $H_2O$ (6×50 mL) and dried over $MgSO_4$. After filtration, evaporation of the solvent left a brown oil (5.7 g, 95% yield): $^1$H NMR ($CDCl_3$): δ 6.96 (s, 2H), 4.33 (s, 4H), 1.57 (m, 12H), 1.33 (m, 12H), 1.10 (m, 12H), 0.91 (t, 18H, $^3$J=6.8 Hz); HRMS (ACPI, $CH_2Cl_2$) m/z: ((M+H)$^+$) calcd for $C_{35}H_{60}S_2O_2Sn_2$, 814.4; found, 815.2.

Example 10i

Synthesis of spiro[4H-cyclopenta[2,1-b:3,4-b']dithiophene-4,2'-[1,3]dioxolane], 2,6-bis-(5-perfluorohexyl carbonylthien-2-yl) (10). A mixture of compound 6 (2.00 g, 2.46 mmol), compound 3 (2.50 g, 4.91 mmol), and Pd[PPh$_3$]$_4$ (0.193 g, 0.167 mmol) in dry DMF (60 mL) was stirred at 90°

C. for 6 h. After 15 min a purple solid precipitated. Filtration of the red solution left the disubstituted product as a dark green solid (2.18 g, 81.04% yield). The solid was washed with ether (3×20 mL) and hexane (3×10 mL), dried overnight in vacuum oven, and purified by gradient sublimation: mp 218° C.; $^1$H NMR (CDCl$_3$): δ 7.88 (2H), 7.32 (4H), 4.39 (4H); $^{19}$F NMR (DMSO) −85.88 (6F), −119.69 (4H), −126.43 (8F), 127.85 (4F), −131.21 (4F); Anal. Calcd for C$_{33}$H$_{10}$F$_{26}$O$_4$S$_4$: C, 36.27; H, 0.92. Found: C, 36.15; H, 1.01; MS (EI, 70 eV) m/z: (M$^+$) calcd for C$_{33}$H$_{10}$F$_{26}$S$_4$O$_4$, 1092.4; found 1092.2.

Example 11

Device Fabrication and Thin Film Characterization. Prime grade n-doped silicon wafers (100) having 300 nm thermally grown oxide (Process Specialties Inc.) were used as device substrates. They were rinsed with water, methanol, and acetone before film deposition. Trimethylsilyl functionalization of the Si/SiO$_2$ surface was carried out by exposing the silicon wafers to hexamethyldisilazane (HMDS) vapor at room temperature in a closed container under nitrogen overnight. Organic compounds were deposited by either vacuum evaporation (pressures <10$^{-5}$ Torr) at a growth rate of 0.2-0.3 Ås$^{-1}$, or by casting films from THF solutions (concentrations 200-400 ppm, 10$^{-4}$-10$^{-2}$ M). Evaporated films were 500 Å thick (as determined by a calibrated in situ quartz crystal monitor), and solution-cast films were variable and thicker, on the order of microns. For solution depositions, a region of the substrate surface (~1-2 cm$^2$) was defined using 3M Novec™ EGC-1700 electronic coating (comparable to the previously used 3M FC-722 product) before casting. The room temperature or warm solution was transferred inside the defined area and allowed to evaporate, with no special care taken to avoid dust in the environment (a clean hood is optional). For FET device fabrication, top-contact electrodes (500 Å) were deposited by evaporating gold (pressure <10$^{-5}$ Torr); channel dimensions were 50/100 μm (L) by 5.0 mm (W). The capacitance of the insulator is 2×10$^{-8}$ F/cm$^2$ for 300 nm SiO$_2$. TFT device measurements were carried out in a customized vacuum probe station (8×10$^{-5}$ Torr) or in air. Coaxial and/or triaxial shielding was incorporated into Signaton probe stations to minimize the noise level. TFT characterization was performed with a Keithly 6430 subfemtoammeter and a Keithly 2400 source meter, operated by a locally written Labview program and GPIB communication.

Example 12

Thin films were analyzed by X-ray film diffractometry (XRD), using standard θ-2θ techniques, with Cu Kα radiation and a monochromator. All θ-2θ scans were calibrated in situ with the reflection of the Si (100) substrates. Films were coated with 3 nm of sputtered Au before analysis by scanning electron microscopy (SEM) using a Hitachi S4500 FE microscope.

Example 13

With reference to examples 13a-13e, and 14, and Scheme 4, all reagents were purchased from commercial sources and used without further purification unless otherwise noted. Ether and tetrahydrofuran were distilled from Na/benzophenone, and carbon disulfide was distilled from calcium hydride prior to use. Conventional Schlenk techniques were used and reactions carried out under N$_2$ unless otherwise noted. The reagents 5,5'-bis(tributylstannyl)-2,2'-dithiophene and 4,4'-dioctyl-2,2'-dithiophene were prepared following known procedures (Wei, Y.; Yang, Y.; Yeh, J.-M. *Chem. Mater.* 1996, 8, 2659).

Scheme 4.

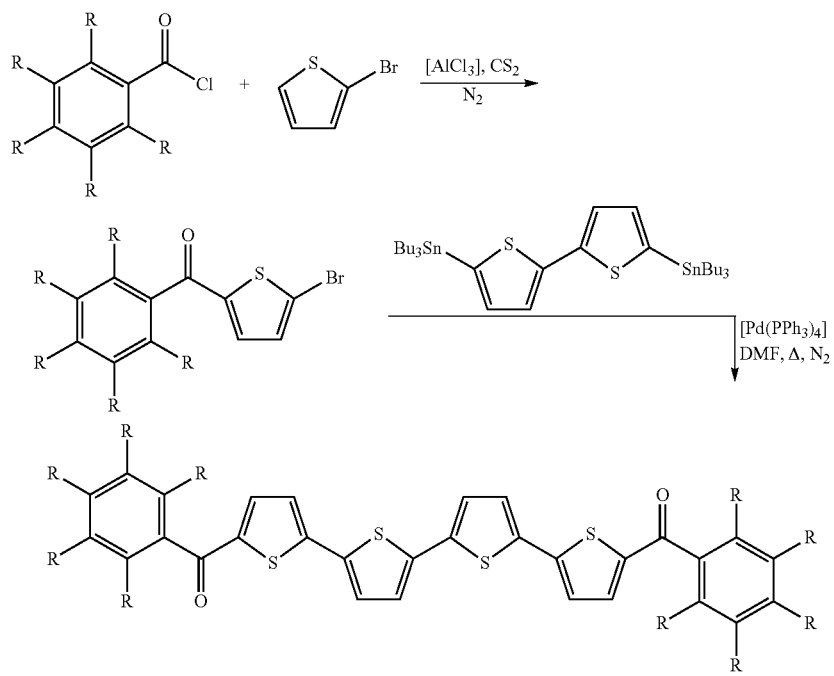

DFCO-4T (1): R = F
DHCO-4T (2): R = H

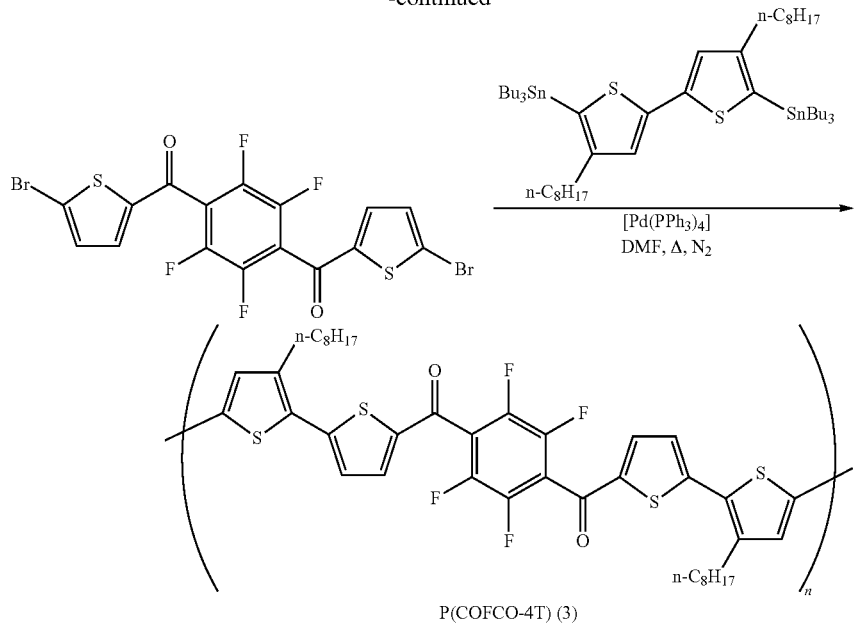

P(COFCO-4T) (3)

Example 13a (2,3,5,6-tetrafluorophenyl) (5-bromothien-2-yl)methanone. To a mixture of perfluorobenzoyl chloride (2.51 g, 10.9 mmol) and 2-bromothiophene (1.86 g, 11.4 mmol) in carbon disulfide (80 mL), aluminum chloride (2.90 g, 21.8 mmol) was added in portions over 10 min with vigorous mechanical stirring. The reaction mixture turned red and was stirred for 2.5 h before being quenched with water (80 mL). The organics were then separated, the aqueous layer extracted with carbon disulfide (3×50 mL), and the combined organics washed with water (3×100 mL) and dried over $MgSO_4$. After filtration, the organics were concentrated in vacuo and the chromatographed on a silica gel column (hexane:ether=9:1) to yield 1.23 g (32%) green crystals. mp 51-54° C.; $^1$H NMR (DMSO): δ 7.78 (d, 2H, $^3$J=3.6 Hz), 7.54 (d, 2H, $^3$J=4.4 Hz); $^{19}$F NMR (DMSO): δ −142.1 (m, 2H), −151.6 (m, 1H), −160.6 (m, 2H) Anal. Calcd for $C_{11}H_2BrF_5OS$: C, 37.00; H, 0.56. Found: C, 37.37; H, 0.83; MS (EI): m/z (%) 355.8 (92) [M$^+$].

Example 13b 5,5'''-bis(perfluorophenylcarbonyl)-2,2':5',2'':5'',2'''-quaterthiophene (DFCO-4T, 1). A mixture of (2,3,5,6-tetrafluorophenyl)(5-bromothien-2-yl)methanone (6) (0.511 g, 1.43 mmol), 5,5'-bis(tributylstannyl)-2,2'-dithiophene (0.532 g, 7.15 mmol), and tetrakis(triphenylphosphine)palladium(0) (0.0250 g, 0.0215 mmol) was degassed with nitrogen three times before 8 mL anhydrous DMF was added. The reaction mixture was heated to 80° C. for 10 h with stirring. A red-brown precipitate formed and upon cooling was collected by filtration, washed with hexanes (3×10 mL) and methanol (3×10 mL). Gradient sublimation (2×) afforded a bright orange crystalline material (0.305 g, 60%) with some crystals suitable for x-ray diffraction. mp 291-294° C.; $^1$H NMR (DMSO): δ 7.87 (d, 2H, $^3$J=3.2 Hz), 7.70 (d, 2H, $^3$J=3.2 Hz), 7.60 (d, 2H, $^3$J=4.4 Hz), 7.54 (d, 2H, $^3$J=4.0 Hz); $^{19}$F NMR (DMSO): δ −142.3 (m), −152.0 (m), −160.7 (m); Anal. Calcd for $C_{30}H_8F_{10}O_2S_4$: C, 50.14; H, 1.12; F, 26.11. Found: C, 50.00, H, 1.30; F, 26.11; MS (EI): m/z (%) 717.8 (100) [M$^+$].

Example 13c (5-bromothien-2-yl)(phenyl)methanone. To a mixture of benzoyl chloride (2.81 g, 20.0 mmol) and 2-bromothiophene (3.42 g, 21.0 mmol) in carbon disulfide (120 mL) aluminum chloride (5.34 g, 40.0 mmol), was added in portions over 10 min with vigorous magnetic stirring. The reaction was next allowed to stir for 2.5 h before being quenched with 100 mL 1 M HCl(aq). The organics were separated, the aqueous layer extracted with carbon disulfide (3×50 mL), and the combined organics washed with water (3×100 mL) and dried over $MgSO_4$. After filtration, the organics were concentrated in vacuo and the residue chromatographed on a silica gel column (hexane:ether=9:1) to yield 5.14 g (96%) of yellow crystals. mp 41-43° C.; $^1$H NMR (CDCl$_3$): δ 7.84 (d, 2H, $^3$J=8.0 Hz), 7.62 (t, 1H, $^3$J=7.2 Hz), 7.52 (t, 2H, $^3$J=7.5 Hz), 7.40 (d, 2H, $^3$J=3.5 Hz), 7.15 (d, 2H, $^3$J=4.0 Hz).

Example 13d 5,5'''-bis(phenylcarbonyl)-2,2':5',2'':5'',2'''-quaterthiophene (DPCO-4T, 2). A mixture of 2-bromo-5-benzoylthiohene (1.07 g, 4.00 mmol), 5,5'-bis(tributylstannyl)-2,2'-dithiophene (1.49 g, 2.00 mmol), and tetrakis(triphenylphosphine)palladium(0) (0.0693 g, 0.0600 mmol) was degassed with nitrogen three times before 20 mL anhydrous DMF was added. The reaction mixture was heated to 80° C. for 15 h with stirring. A deep red precipitate formed and upon cooling and was collected by filtration, then washed with hexanes (3×10 mL) and methanol (3×10 mL). Gradient sublimation (2×) afforded an orange-red crystalline material (0.689 g, 64%) with some crystals suitable for x-ray diffraction. mp 307-310° C.; $^1$H NMR (DMSO): δ 7.85 (2H), 7.84 (2H), 7.67 (4H), 7.59 (2H), 7.53 (2H), 7.48 (1H), 7.44 (1H); Anal. Calcd for $C_{30}H_{18}O_2S_4$: C, 66.88; H, 3.37. Found: C, 66.93; H, 3.42; MS (EI): m/z (%) 538.0 (100) [M$^+$].

Example 13e

P(COFCO-4T) (3). A mixture of 4,4'-dioctyl-5,5'-bis(tributylstannyl)-2,2'-dithiophene (0.969 g, 1.00 mmol), 1,4-bis((5-bromothien-2-yl)carbonyl)-2,3,5,6-tetrafluorobenzene (0.530 g, 1.00 mmol), and tetrakis(triphenylphosphine)palladium(0) (34.7 mg, 0.0300 mmol, 0.03 equiv.) was degassed with nitrogen three times before 10 mL anhydrous DMF was added. The reaction mixture was then heated to 110° C. for an additional 72 h during which time four equal amounts of tetrakis(triphenylphosphine)palladium(0) (34.7 mg, 0.0300 mmol, 0.03 equiv.) were added at intervals of 12 h. After cooling, a red precipitate was isolated by filtration through a 0.45 um filter and washed with methanol (200 mL). The powder was next dissolved in $CHCl_3$, precipitated with methanol, and centrifuged to give black pellets which became translucent red upon drying in a vacuum oven. This process was repeated three times to give 3 (342 mg) as translucent red flakes soluble in toluene, xylenes, trichlorobenzene, thiophene, and THF. This material has a $M_w$ of 15,300 and $M_n$ of 6100 by HT-GPC (140° C., trichlorobenzene, calibrated vs. polystyrene). $^1H$ NMR ($CDCl_3$): δ 7.51 (m, 2H), 7.13 (s, 1H); $^{19}F$ NMR ($CDCl_3$): δ −138.97 (s), −139.03 (s); $^{119}Sn$ NMR δ −4.2 (s); Anal. Calcd for $C_{40}H_{40}F_4O_2S_4$: C, 63.46; H, 5.33. Found: C, 63.20; H, 5.44.

Example 14

Device Fabrication and Thin Film Characterization. Prime grade p-doped silicon wafers (100) having 300 nm thermally grown oxide (Process Specialties Inc. and Montco Silicon Technologies Inc.) were used as device substrates. They were first rinsed with water, methanol, and acetone before film deposition. Trimethylsilyl functionalization of the $Si/SiO_2$ surface was carried out by exposing the silicon wafers to hexamethyldisilazane (HMDS) vapor at room temperature in a closed container under nitrogen overnight. Organic compounds were deposited by either vacuum evaporation (pressures <$10^{-5}$ Torr) at a growth rate of 0.2-0.3 Ås$^{-1}$, or by drop casting films from xylenes solutions (concentrations 200-1000 ppm). Polymer films were spin cast from xylenes or drop cast from a xylenes/triethylamine mixture (7:3 v/v), before being annealed under high vacuum for 1 h at 100° C. Films of polymer and molecule blends were cast from xylenes before annealing under the same conditions. Evaporated films were 500 Å thick (as determined by a calibrated in situ quartz crystal monitor), and solution-cast films were variable and thicker, on the order of microns. For solution depositions, the room temperature or warm solution was transferred onto the temperature controlled substrate and allowed to slowly evaporate, with no special care taken to avoid dust or oxygen in the environment (a clean hood is optional). For FET device fabrication, top-contact electrodes (500 Å) were deposited by evaporating gold (pressure <$10^{-5}$ Torr); channel dimensions were 50/100 μm (L) by 5.0 mm (W). The capacitance of the insulator is $2 \times 10^{-8}$ F/cm$^2$ for 300 nm $SiO_2$. TFT device measurements were carried out in a customized vacuum probe station pumped down to ($8 \times 10^{-6}$ Torr) before being backfilled with Argon or in air. Coaxial and/or triaxial shielding was incorporated into Signatone probe stations to minimize the noise level. TFT characterization was performed with a Keithly 6430 sub-femtoamp meter and a Keithly 2400 source meter, operated by a locally written Labview program and GPIB communication. Thin films were analyzed by wide-angle X-ray film diffractometry (WAXRD) on a Rikagu ATX-G using standard θ-2θ techniques, with Cu Kα radiation and a monochromator. All θ-2θ scans were calibrated in situ with the reflection of the Si (100) substrates.

We claim:

1. A semiconductor compound of the formula:

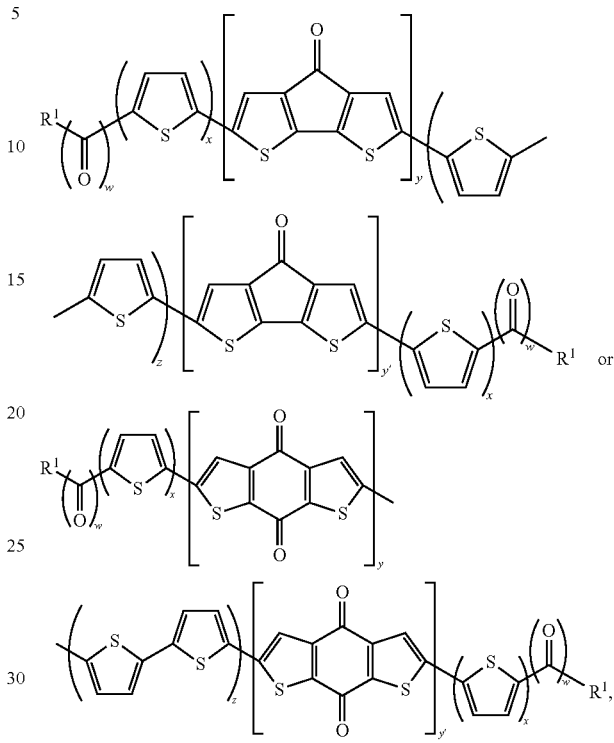

wherein $R^1$ is selected from H, alkyl, fluorosubstituted alkyl, aryl and fluorosubstituted aryl moieties, said alkyl and fluorosubstituted alkyl moieties ranging from $C_2$ to $C_{10}$; each said x is an integer independently ranging from 0 to 4; each of y and y' is an integer independently selected from 0 and 1; z is an integer selected from 0 and integers greater than 0; and each said w is an integer independently selected from 0 and 1, wherein at least one of said x and z is 1, and at least one of y and y' is 1.

2. The compound of claim 1 having the formula:

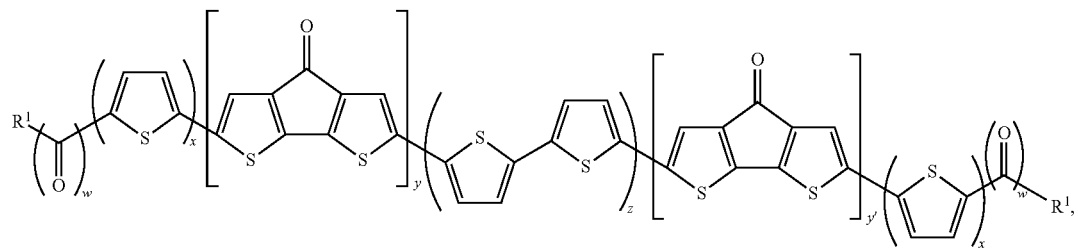

wherein $R^1$ is selected from alkyl, fluorosubstituted alkyl, phenyl and fluorosubstituted phenyl moieties, wherein w, x, y, y', and z are as defined in claim 1.

3. The compound of claim 2, wherein each said x is 1, y is 1, z and y' are 0, and each said w is 1.

4. The compound of claim 3, wherein $R^1$ is selected from alkyl and perfluoroalkyl, said alkyl and fluorosubstituted alkyl moieties ranging from $C_2$ to $C_{10}$.

5. The compound of claim 4, wherein $R^1$ is selected from hexyl and perfluorohexyl.

6. The compound of claim 1 having the formula:

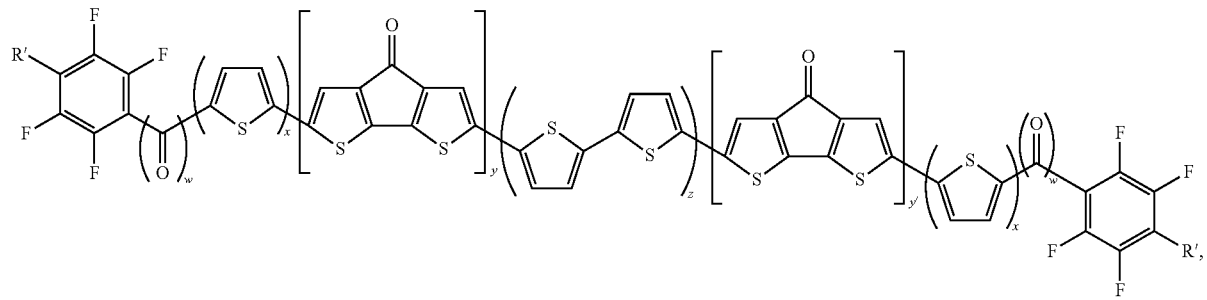

wherein each of x, y, and w is 1; z and y' are 0, and R' is selected from H and F.

7. The compound of claim 6, wherein R' is F.

8. The compound of claim 1 having the formula:

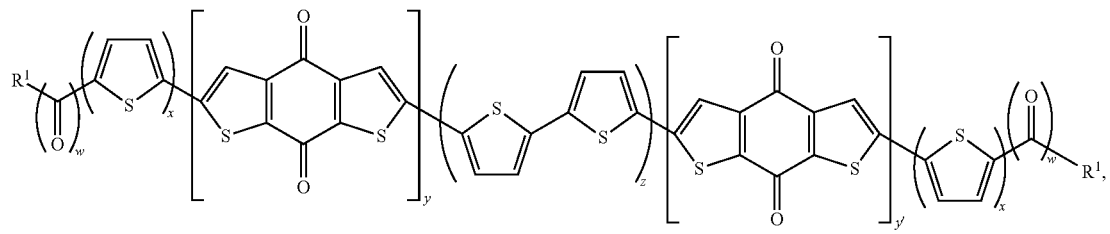

wherein each of x, y, and w is 1; z and y' are 0, and $R^1$ is selected from alkyl, fluorosubstituted alkyl, phenyl and fluorosubstituted phenyl moieties, said alkyl and fluorosubstituted alkyl moieties ranging from $C_2$ to $C_{10}$.

9. An organic field effect transistor device comprising a semiconductor component comprising one or more compounds of claim 1.

10. An organic field effect transistor device comprising a semiconductor component fabricated with a composition comprising one or more compounds of claim 1 in a solvent and a polymer capable of enhancing the solubility of said one or more compounds in the solvent.

11. An organic field effect transistor device comprising a semiconductor component fabricated with a composition comprising a compound of claim 1 and a compound of the formula:

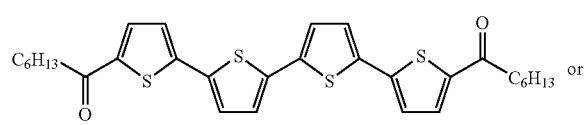

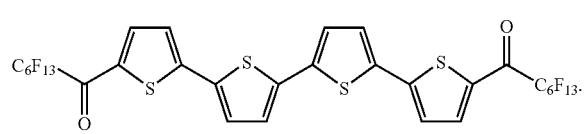

12. A compound of the formula

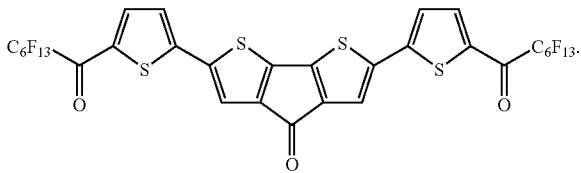

13. An organic field effect transistor device comprising a semiconductor component comprising the compound of claim 12.

14. An organic field effect transistor device comprising a semiconductor component fabricated with a composition comprising the compound of claim 12 and a compound of the formula:

15. An organic field effect transistor device comprising a semiconductor component comprising a compound having the formula:

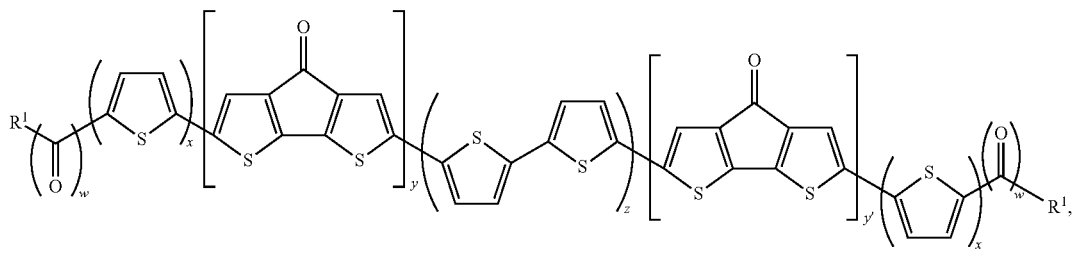

wherein R¹ is selected from H, alkyl, fluorosubstituted alkyl, aryl and fluorosubstituted aryl moieties, said alkyl and fluorosubstituted alkyl moieties ranging from $C_2$ to $C_{10}$; each said x is an integer independently ranging from 0 to 4; each of y and y' is an integer independently selected from 0 and 1; z is an integer selected from 0 and integers greater than 0; and each said w is an integer independently selected from 0 and 1, wherein at least one of said x and z is 1, and at least one of y and y' is 1.

16. The device of claim 15, wherein each said x is 1, y is 1, z and y' are 0, and each said w is 1.

17. The device of claim 16, wherein R¹ is selected from alkyl and perfluoroalkyl, said alkyl and fluorosubstituted alkyl moieties ranging from $C_2$ to $C_{10}$.

18. The device of claim 15, wherein each of x, y, and w is 1; z and y' are 0, and R¹ is selected from phenyl and fluorosubstituted phenyl moieties.

19. An organic field effect transistor device comprising a semiconductor component comprising a compound of claim 6.

20. An organic field effect transistor device comprising a semiconductor component comprising a compound of claim 6 and a compound of the formula:

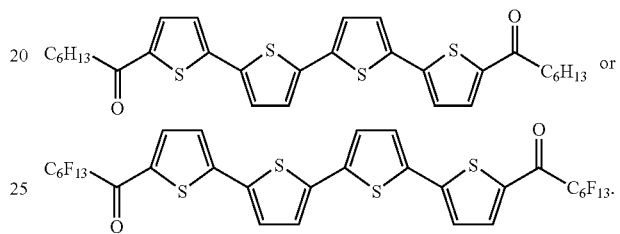

* * * * *